(12) United States Patent
Chang et al.

(10) Patent No.: US 11,814,627 B2
(45) Date of Patent: Nov. 14, 2023

(54) CIRCULAR RNAS AND THEIR USE IN IMMUNOMODULATION

(71) Applicants: THE BOARD OF TRUSTEES OF THE LELAND STANFORD JUNIOR UNIVERSITY, Stanford, CA (US); EMORY UNIVERSITY, Atlanta, GA (US)

(72) Inventors: Howard Y. Chang, Stanford, CA (US); Ye Grace Chen, Stanford, CA (US); Bali Pulendran, Stanford, CA (US); Sudhir Kasturi, Atlanta, GA (US)

(73) Assignees: THE BOARD OF THE LELAND STANFORD JUNIOR UNIVERSITY, Stanford, CA (US); EMORY UNIVERSITY, Atlanta, GA (US)

( * ) Notice: Subject to any disclaimer, the term of this patent is extended or adjusted under 35 U.S.C. 154(b) by 570 days.

(21) Appl. No.: 16/311,770

(22) PCT Filed: Jun. 15, 2017

(86) PCT No.: PCT/US2017/037702
§ 371 (c)(1),
(2) Date: Dec. 20, 2018

(87) PCT Pub. No.: WO2017/222911
PCT Pub. Date: Dec. 28, 2017

(65) Prior Publication Data
US 2019/0345503 A1 Nov. 14, 2019

Related U.S. Application Data

(60) Provisional application No. 62/352,471, filed on Jun. 20, 2016.

(51) Int. Cl.
*A61K 48/00* (2006.01)
*C12N 15/67* (2006.01)
(Continued)

(52) U.S. Cl.
CPC .............. *C12N 15/67* (2013.01); *A61K 39/39* (2013.01); *C12N 15/117* (2013.01);
(Continued)

(58) Field of Classification Search
CPC .......................................................... A61K 48/00
See application file for complete search history.

(56) References Cited

U.S. PATENT DOCUMENTS 5,766,903 A  6/1998 Sarnow et al.
5,773,244 A †  6/1998 Ares
(Continued)

FOREIGN PATENT DOCUMENTS

WO   WO-2007044394 A2 *  4/2007  ......... A61K 39/0007
WO   WO-2010037539 A1 *  4/2010  ......... A61K 39/0011
(Continued)

OTHER PUBLICATIONS

Roponen et al., Toll-like receptor 7 function is reduced in adolescents with asthma (Eur Resp J, 2010, 35:64-71) (Year: 2010).*
(Continued)

*Primary Examiner* — Arthur S Leonard
(74) *Attorney, Agent, or Firm* — Casimir Jones, S.C.; Tanya A. Arenson

(57) ABSTRACT

Compositions and methods of modulating an innate immune response with circular RNAs are disclosed. In particular, the disclosure relates to methods for modifying an RNA by circularization and the use of circular RNAs generated with exogenous introns to stimulate an innate immune response or circular RNAs generated with endogenous introns to prevent immune recognition of foreign RNA.

14 Claims, 16 Drawing Sheets

Specification includes a Sequence Listing.

(51) Int. Cl.
  *A61K 39/39* (2006.01)
  *C12N 15/117* (2010.01)
  *A61K 39/00* (2006.01)
(52) U.S. Cl.
  CPC .............. *A61K 2039/55555* (2013.01); *C12N 2310/17* (2013.01); *C12N 2310/532* (2013.01)

(56) References Cited

U.S. PATENT DOCUMENTS

| | | | |
|---|---|---|---|
| 2012/0021043 A1* | 1/2012 | Kramps | A61P 33/14 424/282.1 |
| 2016/0082092 A1 | 3/2016 | Ingmar et al. | |
| 2016/0083747 A1* | 3/2016 | Kruse | C12N 15/115 514/44 R |
| 2018/0044739 A1 | 2/2018 | Weinbaum et al. | |
| 2018/0169146 A1† | 6/2018 | Goldberg | |
| 2018/0214537 A1* | 8/2018 | Mutzke | A61K 39/12 |
| 2019/0345503 A1† | 11/2019 | Chang | |

FOREIGN PATENT DOCUMENTS

| | | | |
|---|---|---|---|
| WO | WO20100084371 A1 | | 7/2010 |
| WO | WO20140082644 A1 | | 6/2014 |
| WO | WO2016011222 A2 | | 1/2016 |
| WO | WO2017081082 A2 | | 5/2017 |
| WO | WO2017222911 A1 | | 12/2017 |
| WO | WO2020023655 A1 | | 1/2020 |
| WO | WO2020/181013 | † | 9/2020 |
| WO | WO2020219563 A1 | | 10/2020 |
| WO | WO2020/237227 | † | 11/2020 |

OTHER PUBLICATIONS

Szabo et al., TLR ligands upregulate RIG-I expression in human plasmacytoid dendritic cells in a type I IFN-independent manner (Immuno Cell Bio, 2014, 1-8) (Year: 2014).*

Colak et al. RNA and Imidazoquinolines Are Sensed by Distinct TLR7/8 Ectodomain Sites Resulting in Functionally Disparate Signaling Events (J Immuno, 2014, 192:5963-5973) (Year: 2014).*

Baranick et al., "Splicing mediates the activity of four putative cellular internal ribosome entry sites." Proc Natl Acad Sci U S A. Mar 25, 2008;105(12):4733-8.

Bert et al., "Assessing IRES activity in the HIF-1alpha and other cellular 5' UTRs." RNA. Jun. 2006;12(6):1074-83.

Brito et al., "A cationic nanoemulsion for the delivery of next-generation RNA vaccines." Mol Ther. Dec. 2014;22(12):2118-29.

Chen et al., "Sensing Self and Foreign Circular RNAs by Intron Identity." Mol Cell. Jul. 20, 2017;67(2):228-238.e5.

Chu et al., "Systematic discovery of Xist RNA binding proteins." Cell. Apr. 9, 2015;161(2):404-16.

Dobrikova et al., "Activity of a type 1 picornavirus internal ribosomal entry site is determined by sequences within the 3' nontranslated region." Proc Natl Acad Sci U S A. Dec. 9, 2003;100(25):15125-30.

Dolinnaya et al., "Oligonucleotide circularization by template-directed chemical ligation." Nucleic Acids Res. Nov. 25, 1993;21(23):5403-7.

Dolinnaya et al., "The use of BrCN for assembling modified DNA duplexes and DNA-RNA hybrids; comparison with water-soluble carbodiimide." Nucleic Acids Res. Jun. 11, 1991;19(11):3067-72.

Fedorova et al. "Cyanogen bromide-induced chemical ligation: Mechanism and optimization of the reaction conditions." Nucleosides, Nucleotides & Nucleic Acids 15.6 (1996): 1137-1147.

Ford et al., "Synthesis of circular RNA in bacteria and yeast using RNA cyclase . ribozymes derived from a group I intron of phage T4." Proc Natl Acad Sci U S A. Apr. 12, 1994;91(8):3117-21.

Garlapati et al., "Identification of a novel internal ribosome entry site in giardiavirus that extends to both sides of the initiation codon." J Biol Chem. Jan. 30, 2004;279(5):3389-97.

Gurtu et al., "IRES bicistronic expression vectors for efficient creation of stable mammalian cell lines." Biochem Biophys Res Commun. Dec. 4, 1996;229(1):295-8.

Hansen et al., "Natural RNA circles function as efficient microRNA sponges." Nature. Mar. 21, 2013;495(7441):384-8.

Haussecker et al., "Capped small RNAs and MOV10 in human hepatitis delta virus replication." Nat Struct Mol Biol. Jul. 2008;15(7):714-21.

Hornung et al., "5'-Triphosphate RNA is the ligand for RIG-I." Science. Nov. 10, 2006;314(5801):994-7.

International Search Report of related PCT/US2017/037702, dated Oct. 27, 2017, 12 pages.

Jang et al., "Initiation of protein synthesis by internal entry of ribosomes into the 5' nontranslated region of encephalomyocarditis virus Rna in vivo." J Virol. Apr. 1989;63(4):1651-60.

Jeck et al., "Circular RNAs are abundant, conserved, and associated with ALU repeats." RNA. Feb. 2013;19(2):141-57.

Jeck et al., "Detecting and characterizing circular RNAs." Nat Biotechnol. May 2014;32(5):453-61.

Kato et al., "Cell type-specific involvement of RIG-I in antiviral response." Immunity. Jul. 2005;23(1):19-28.

Kato et al., "Length-dependent recognition of double-stranded ribonucleic acids by retinoic acid-inducible gene-I and melanoma differentiation-associated gene 5." J Exp Med. Jul. 7, 2008;205(7):1601-10.

Kaufman et al., "Improved vectors for stable expression of foreign genes in mammalian cells by use of the untranslated leader sequence from EMC virus." Nucleic Acids Res. Aug. 25, 1991;19(16):4485-90.

Kramps et al., "Messenger RNA-based vaccines: progress, challenges, applications." Wiley Interdiscip Rev RNA. Nov.-Dec. 2013;4(6):737-49.

Kobayashi et al., "Improved dicistronic mRNA expression vectors for efficient selection of transfectants highly expressing foreign genes." Biotechniques. Sep. 1996;21(3):398-402.

Kos et al., "The hepatitis (delta) virus possesses a circular RNA." Nature. Oct. 9-15, 1986;323(6088):558-60.

Kramer et al., "Combinatorial control of Drosophila circular RNA expression by intronic repeats, hnRNPs, and SR proteins." Genes Dev. Oct. 15, 2015;29(20):2168-82.

Liang et al., "Short intronic repeat sequences facilitate circular RNA production." Genes Dev. Oct. 15, 2014;28(20):2233-47.

Martin et al., "Translation of the human angiotensin II type 1 receptor mRNA is mediated by a highly efficient internal ribosome entry site." Mol Cell Endocrinol. Dec. 30, 2003;212(1-2):51-61.

Martineau et al., "Internal ribosome entry site structural motifs conserved among mammalian fibroblast growth factor 1 alternatively spliced mRNAs." Mol Cell Biol. Sep. 2004;24(17):7622-35.

Memczak et al., "Circular RNAs are a large class of animal RNAs with regulatory potency." Nature. Mar. 21, 2013;495(7441):333-8.

Molinie et al., "m(6)A-LAIC-seq reveals the census and complexity of the m(6)A epitranscriptome." Nat Methods. Aug. 2016;13(8):692-8.

Mosser et al., "Use of a dicistronic expression cassette encoding the green fluorescent protein for the screening and selection of cells expressing inducible gene products." Biotechniques. Jan. 1997;22(1):150-161.

Pedersen et al., "Human insulin-like growth factor II leader 2 mediates internal initiation of translation." Biochem J. Apr. 1, 2002;363(Pt 1):37-44.

Petkovic et al., "RNA circularization strategies in vivo and in vitro." Nucleic Acids. Res. Feb. 27, 2015;43(4):2454-65.

Puttaraju et al., "Generation of nuclease resistant circular RNA decoys for HIV-Tat and HIV-Rev by autocatalytic splicing." Nucleic Acids Symp Ser. 1995;(33):49-51.

Ramesh et al., "High-titer bicistronic retroviral vectors employing foot-and-mouth disease virus internal ribosome entry site." Nucleic Acids Res. Jul. 15, 1996;24(14):2697-700.

Rees et al., "Bicistronic vector for the creation of stable mammalian cell lines that predisposes all antibiotic-resistant cells to express recombinant protein." Biotechniques. Jan. 1996;20(1):102-4, 106, 108-10.

(56) References Cited

OTHER PUBLICATIONS

Salzman et al., "Circular RNAs are the predominant transcript isoform from hundreds of human genes in diverse cell types." PLoS One. 2012;7(2):e30733. 12 pages.
Sanger et al., "Viroids are single-stranded covalently closed circular RNA molecules existing as highly base-paired rod-like structures." Proc Natl Acad Sci U S A. Nov. 1976;73(11):3852-6.
Savva et al. "Reprogramming, Circular Reasoning and Self versus Non-self: One-Stop Shopping with RNA Editing." Front Genet. Jun. 7, 2016;7:100., 8 pages.
Schlake et al. "Developing mRNA-vaccine technologies." RNA Biol. Nov. 2012;9(11):1319-30.
Sokolova et al., "Chemical reactions within DNA duplexes Cyanogen bromide as an effective oligodeoxyribonucleotide coupling agent." FEBS Lett. May 9, 1988;232(1):153-5.
Spitale et al., "Structural imprints in vivo decode RNA regulatory mechanisms." Nature. Mar. 26, 2015;519(7544):486-90.
Stein et al., "Translation of vascular endothelial growth factor mRNA by internal ribosome entry: implications for translation under hypoxia." Mol Cell Biol. Jun. 1998;18(6):3112-9.
Tomari et al., "RISC assembly defects in the *Drosophila* RNAi mutant armitage." Cell. Mar. 19, 2004;116(6):831-41.
Warren et al., "Highly efficient reprogramming to pluripotency and directed differentiation of human cells with synthetic modified mRNA." Cell Stem Cell. Nov. 5, 2010;7(5):618-30.
Yang et al., "Extensive translation of circular RNAs driven by N6-methyladenosine." Cell Res. May 2017;27(5):626-641.
Ying et al., "Cancer therapy using a self-replicating RNA vaccine." Nat Med. Jul. 1999;5(7):823-7.
European Search Report for related EP17815958.8, dated Dec. 5, 2019, 12 pages.
Ahmad et al., "Breaching Self-Tolerance to Alu Duplex RNA Underlies MDA5-Mediated Inflammation." Cell. Feb. 8, 2018;172(4):797-810.e13.
Australian Examination Report for AU Application No. 2017280943, dated May 3, 2022, 5 pages.
Batista et al., "m(6)A RNA modification controls cell fate transition in mammalian embryonic stem cells." Cell Stem Cell. Dec. 4, 2014;15(6):707-19.
Chandry et al., "Activation of a cryptic 5' splice site in the upstream exon of the phage T4 td transcript: exon context, missplicing, and mRNA deletion in a fidelity mutant." Genes Dev. Nov. 1987;1(9):1028-37.
Chen et al., "N6-Methyladenosine Modification Controls Circular RNA Immunity". Mol Cell. Oct. 3, 2019;76(1):96-109.e9.
Chen et al., "Pervasive functional translation of noncanonical human open reading frames." Science. Mar. 6, 2020;367(6482):1140-1146.
Crooke et al., "RNA-Targeted Therapeutics." Cell Metab. Apr. 3, 2018,27(4):714-739.
Devarkar et al., "Structural basis for m7G recognition and 2'-O-methyl discrimination in capped RNAs by the innate immune receptor RIG-I." Proc Natl Acad Sci U S A. Jan. 19, 2016;113(3):596-601.
Dominissini et al., "Topology of the human and mouse m6A RNA methylomes revealed by m6A-seq." Nature. Apr. 29, 2012;485(7397):201-6.
Durbin et al., "RNAs Containing Modified Nucleotides Fail to Trigger RIG-I Conformational Changes for Innate Immune Signalingm." Bio. 2016. 7: e00833-00816. 11 pages.
Edupuganti et al., "N 6-methyladenosine (m 6 A) recruits and repels proteins to regulate mRNA homeostasis." Nat Struct Mol Biol. Oct. 2017;24(10):870-878.
Glazar et al., "circBase: a database for circular RNAs." RNA. Nov. 2014;20(11):1666-70.
Holdt et al., "Circular RNAs as Therapeutic Agents and Targets." Front Physiol. Oct. 9, 2018;9:1262.
International Search Report and Written Opinion for PCT/US20/47995, dated Jan. 26, 2021. 9 pages.
International Search Report and Written Opinion for PCT/US2021/039127,dated Dec. 13, 2021. 17 pages.
Jiang et al., "A Quantitative Proteome Map of the Human Body." Cell. Oct. 1, 2020;183(1):269-283.e19.
Jiang et al., "Ubiquitin-induced oligomerization of the RNA sensors RIG-I and MDA5 activates antiviral innate immune response." Immunity. Jun. 29, 2012;36(6):959-73.
Ke et al., "A majority of m6A residues are in the last exons, allowing the potential for 3' UTR regulation." Genes Dev. Oct. 1, 2015;29(19):2037-53.
Krutzfeldt et al., "Silencing of microRNAs in vivo with 'antagomirs'." Nature. Dec. 1, 2005;438(7068):685-9.
Li et al., "Coordinated circRNA Biogenesis and Function with NF90/NF110 in Viral Infection." Mol Cell. Jul. 20, 2017;67(2):214-227.e7.
Liu et al., "Structure and Degradation of Circular RNAs Regulate PKR Activation in Innate Immunity."Cell. May 2, 2019;177(4):865-880.e21.
Meyer et al., "Comprehensive analysis of mRNA methylation reveals enrichment in 3' UTRs and near stop codons." Cell. Jun. 22, 2012;149(7):1635-46.
Mokrejš et al., "IRESite—a tool for the examination of viral and cellular internal ribosome entry sites." Nucleic Acids Res. Jan. 2010;38(Database issue):D131-6.
Olexiouk et al., "An update on sORFs.org: a repository of small ORFs identified by ribosome profiling." Nucleic Acids Res. Jan. 4, 2018;46(D1):D497-D502.
Peisley et al., "RIG-I forms signaling-competent filaments in an ATP-dependent, ubiquitin-independent manner." Mol Cell. Sep. 12, 2013;51(5):573-83.
Peisley et al., "Structural basis for ubiquitin-mediated antiviral signal activation by RIG-I." Nature. May 1, 2014;509(7498):110-4.
Perriman et al., "Circular mRNA can direct translation of extremely long repeating-sequence proteins in vivo." RNA. Sep. 1998;4(9):1047-54.
Pisarev et al., "Ribosomal position and contacts of mRNA in eukaryotic translation initiation complexes." EMBO J. Jun. 4, 2008;27(11):1609-21.
Qi et al., "Melting temperature highlights functionally important RNA structure and sequence elements in yeast mRNA coding regions." Nucleic Acids Res. Jun. 2, 2017;45(10):6109-6118.
Roundtree et al., "Dynamic RNA Modifications in Gene Expression Regulation." Cell. Jun. 15, 2017;169(7):1187-1200.
Rybak-Wolf et al., "Circular RNAs in the Mammalian Brain Are Highly Abundant, Conserved, and Dynamically Expressed." Mol Cell. Jun. 4, 2015;58(5):870-85.
Schlee et al., "Recognition of 5' triphosphate by RIG-I helicase requires short blunt double-stranded RNA as contained in panhandle of negative-strand virus." Immunity. Jul. 17, 2009;31(1):25-34.
Vandivier et al., "The Conservation and Function of RNA Secondary Structure in Plants." Annu Rev Plant Biol. Apr. 29, 2016;67:463-88.
Wang et al., "N6-methyladenosine-dependent regulation of messenger RNA stability." Nature. Jan. 2, 2014;505(7481):117-20.
Weingarten-Gabbay et al., "Comparative genetics. Systematic discovery of cap-independent translation sequences in human and viral genomes." Science. Jan. 15, 2016;351(6270):aad4939. 15 pages.
Wesselhoeft et al., "Engineering circular RNA for potent and stable translation in eukaryotic cells." Nat Commun. Jul. 6, 2018;9(1):2629. 10 pages.
Wesselhoeft et al., "RNA Circularization Diminishes Immunogenicity and Can Extend Translation Duration In Vivo." Mol Cell. May 2, 2019;74(3):508-520.e4.
Wu et al., "How RIG-I like receptors activate MAVS." Curr Opin Virol. Jun. 2015;12:91-8.
Xia et al., "CSCD: a database for cancer-specific circular RNAs." Nucleic Acids Res. Jan. 4, 2018;46(D1):D925-D929.
Yao et al., "ZKSCAN1 gene and its related circular RNA (circZKSCAN1) both inhibit hepatocellular carcinoma cell growth, migration, and invasion but through different signaling pathways." Mol Oncol. Apr. 2017;11(4):422-437.
Zarnegar et al., "irCLIP platform for efficient characterization of protein-RNA interactions." Nat Methods. Jun. 2016;13(6):489-92.

(56) References Cited

OTHER PUBLICATIONS

Zeng et al., "Reconstitution of the RIG-I pathway reveals a signaling role of unanchored polyubiquitin chains in innate immunity." Cell. Apr. 16, 2010;141(2):315-30.

Zhou et al., "Genome-Wide Maps of m6A circRNAs ldentify Widespread and Cell-Type-Specific Methylation Patterns that Are Distinct from mRNAs." Cell Rep. Aug. 29, 2017;20(9):2262-2276.

Ellese Marie Carmona, Circular RNA: Design Criteria for Optimal Therapeutical Utility, 1 to 118, Jan. 2019, Harvard, US.†

R. Alexander Wesselhoeft, Circularization Diminishes Immunogenicity and Can Extend Translation Duration In Vivo, 508 to 520, Mar. 19, 2019, Molecular Cell.†

Koji Onomoto, et al., Regulation of RIG-I-like receptor-mediated signaling: interaction between host and viral factors, 539 to 555, Jan. 18, 2021, Nature.†

Zubaida Hassan, Functions and Implications of Circular RNAs in Antiviral Immunity, 602 to 615, Jul. 22, 2019, Scientific Research Publishing.†

Lan Yang et al., Circular RNAs and Their Emerging Roles in Immune Regulation, 1 to 10, Dec. 18, 2018, Frontiers.†

Man Wang et al., Circular RNAs: A novel type of noncoding RNA and their potential implications in antiviral immunity, 1497 to 1506, Nov. 2 2017, Ivyspring.†

Cristhian Candena and Sun Hur, Antiviral Immunity and Circular RNA: No End in Sight, 1 to 5, Jul. 20, 2017, Molecular Cell.†

Y. Grace Chen et al., Sensing Selfand Foreign Circular RNAs by Intron Identity, 1 to 29, Jun. 15, 2017, Molecular Cell.†

Jan Rehwinkel and Michaela U. Gack, RIG-I-like receptors: their regulation and roles in RNA sensing, 537 to 551, Mar. 13, 2020, Nature.†

\* cited by examiner
† cited by third party (SEQ ID NO: 38)

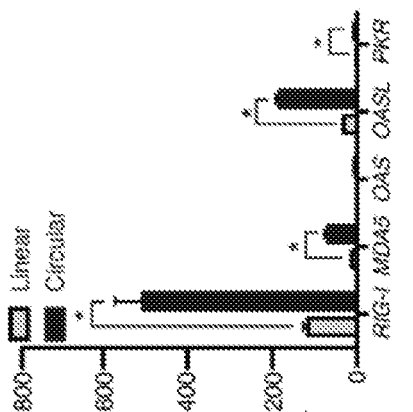
FIG. 2A
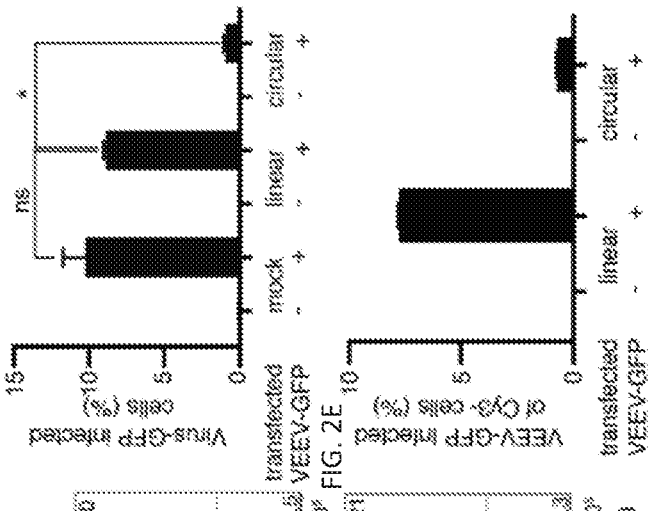
FIG. 2B
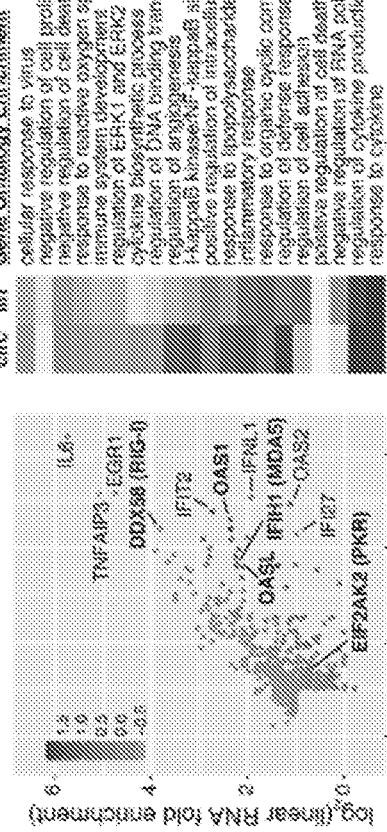
FIG. 2C
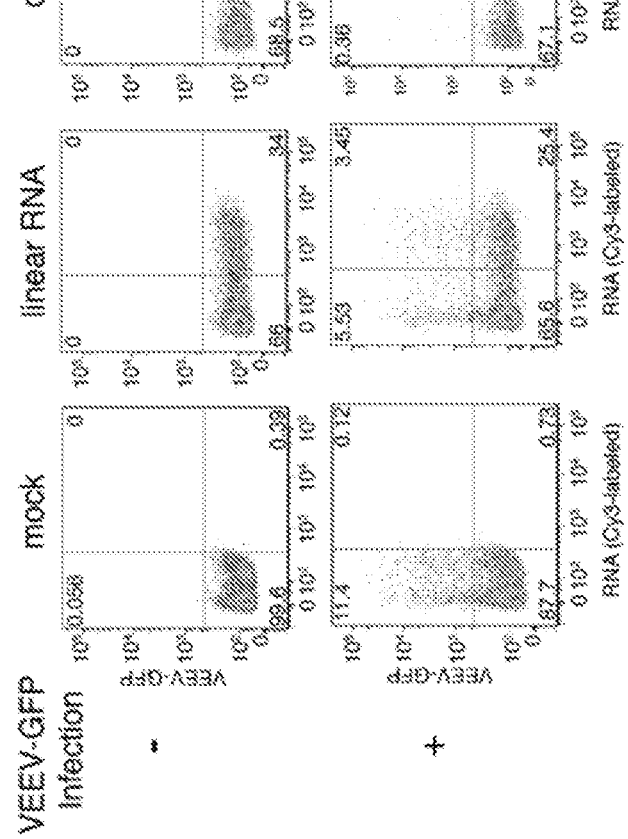
FIG. 2D
FIG. 2E

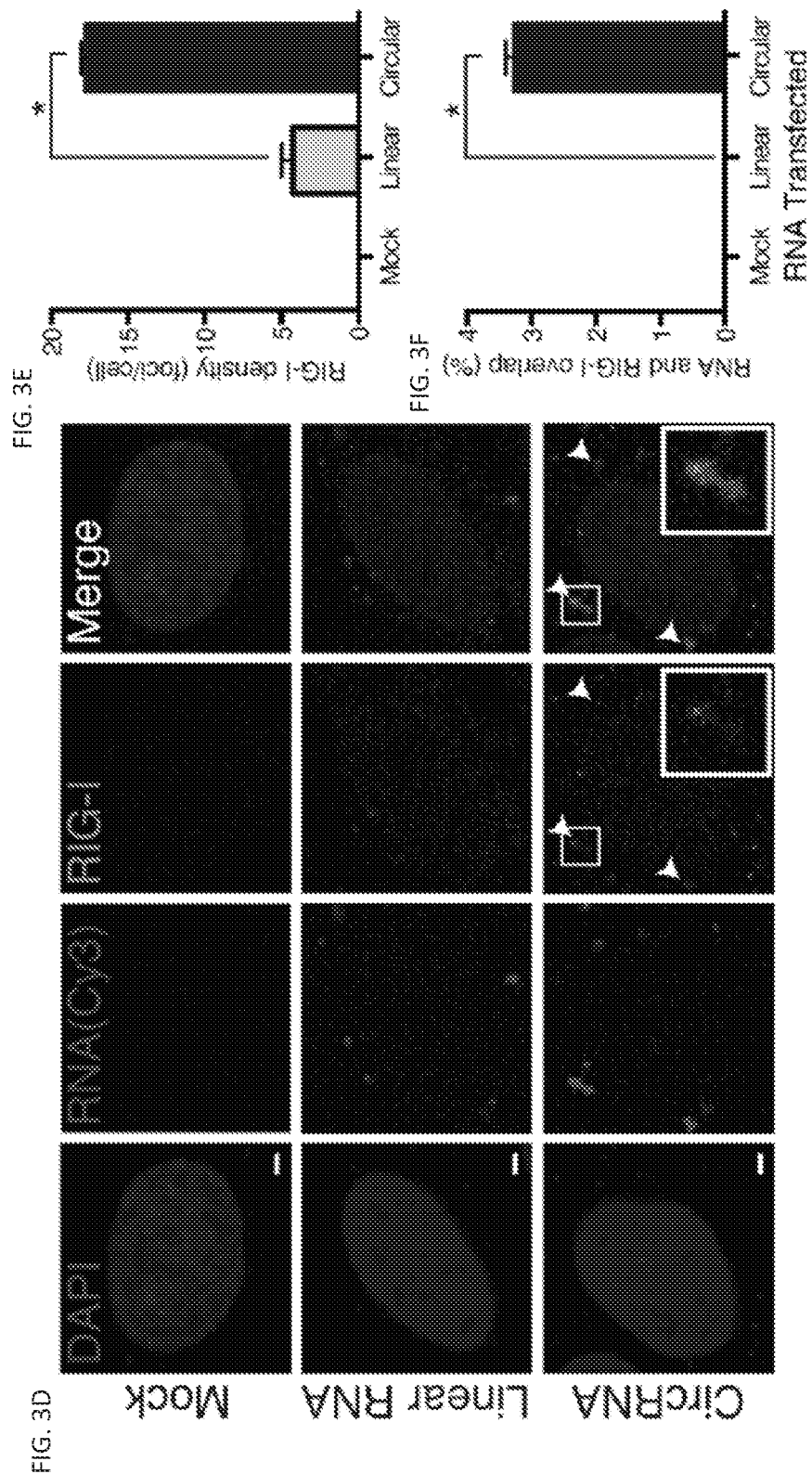

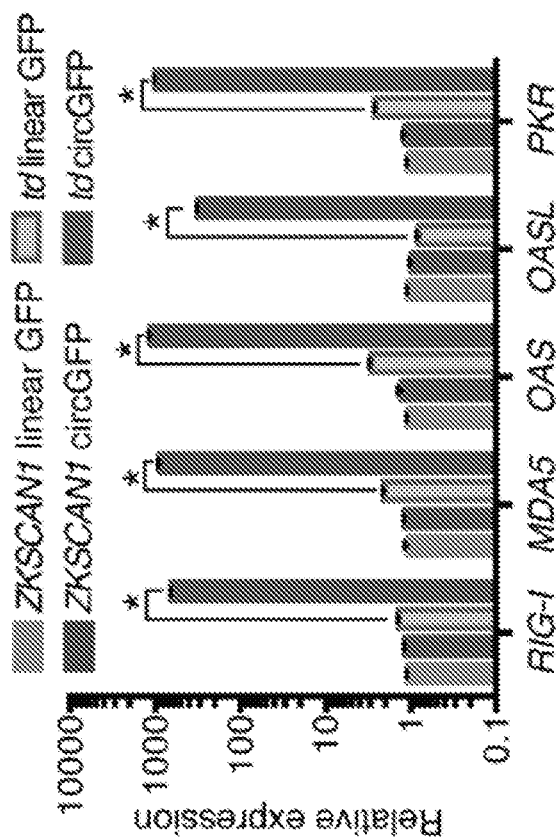
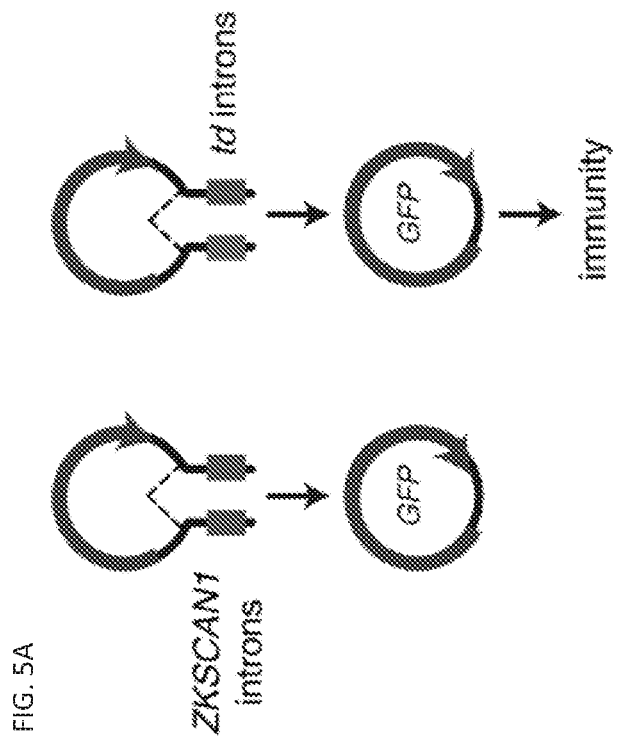
FIG. 5A

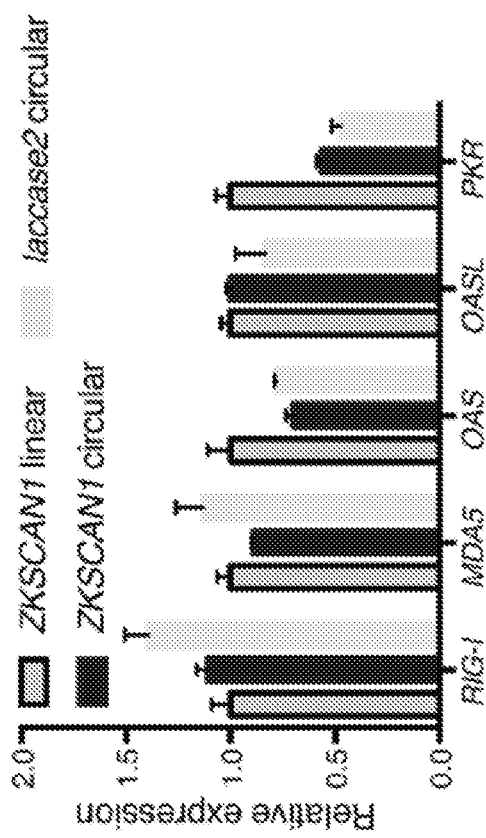
FIG. 5B
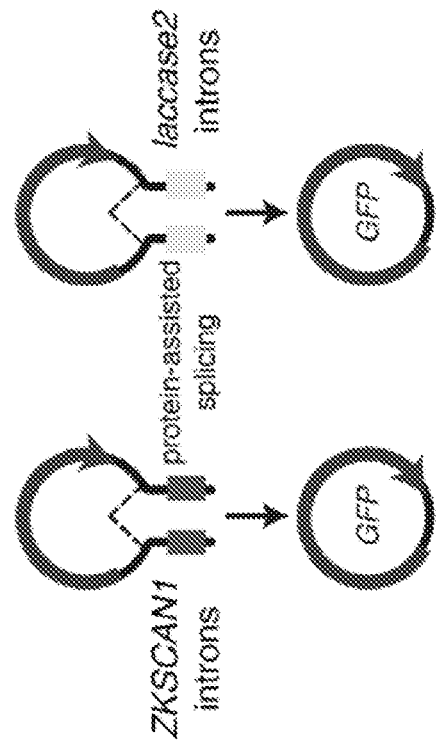
FIG. 5C
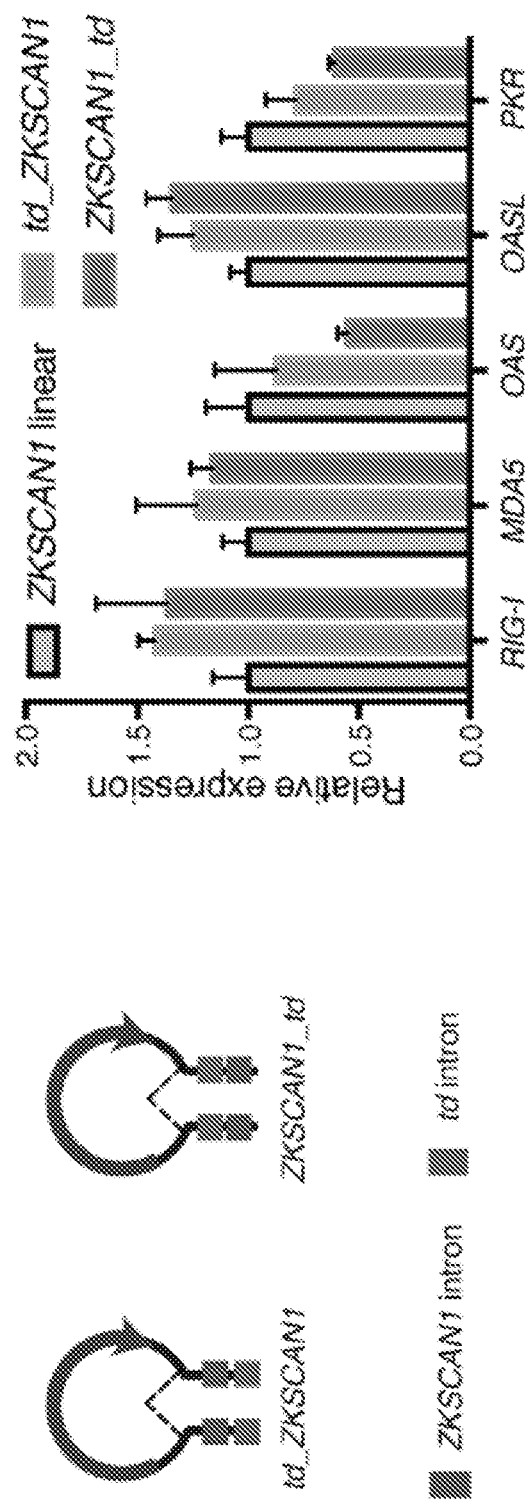

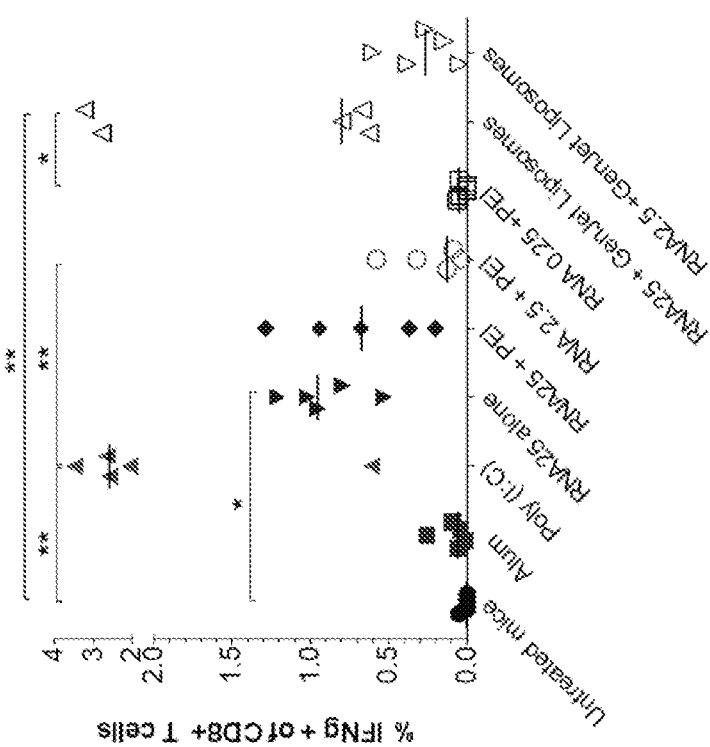
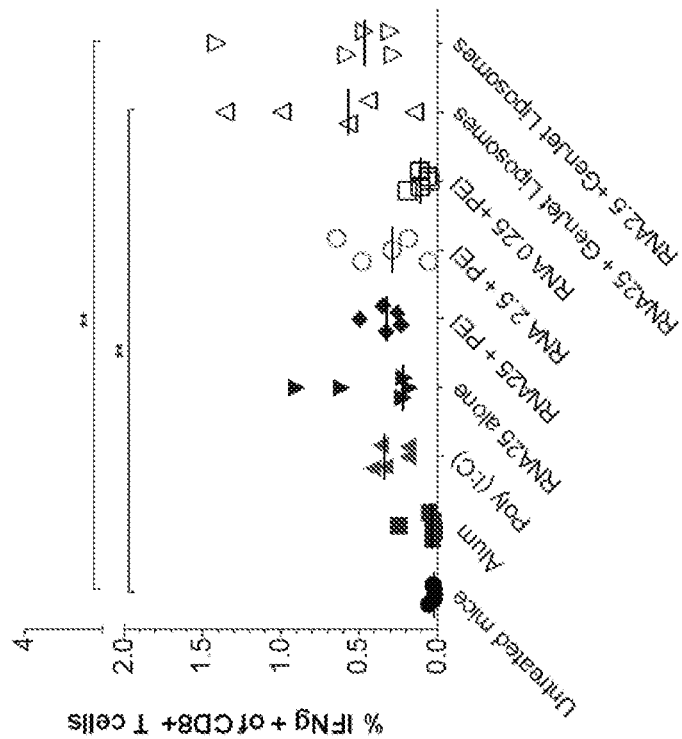
FIGURE 9

FIGURE 11
RNA only comparison
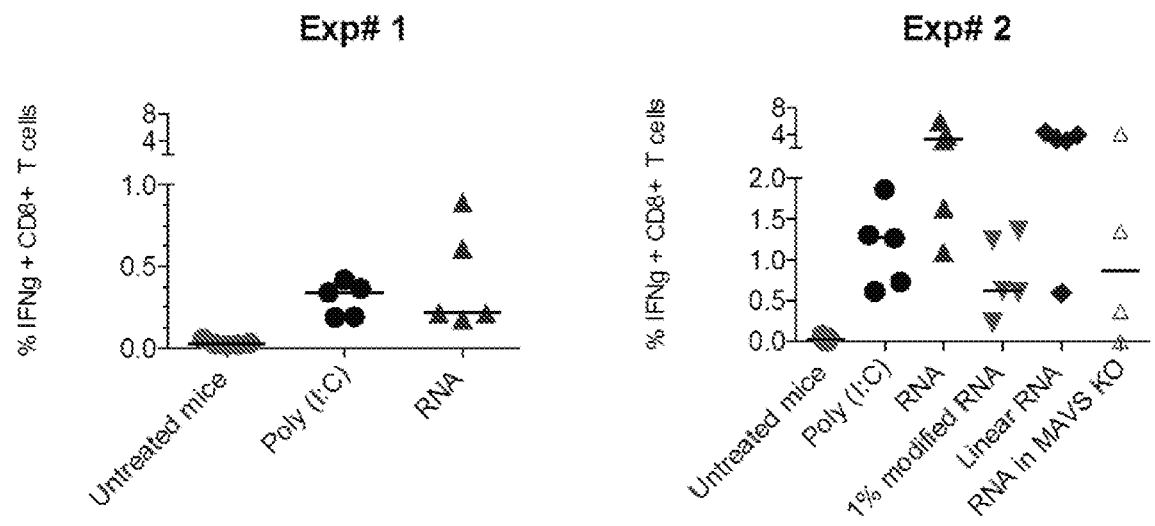
RNA with delivery vehicles only comparison
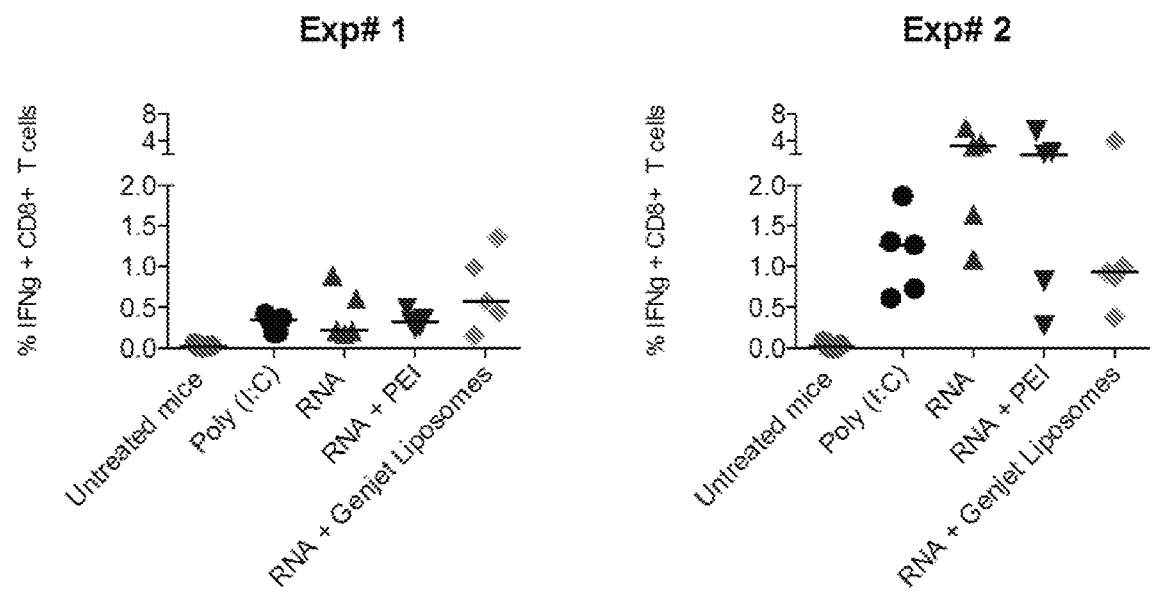

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Linear GFP forward primer

```
<400> SEQUENCE: 1
actacctgag cacccagtcc                                              20

<210> SEQ ID NO 2
<211> LENGTH: 20
<212> TYPE: DNA
<213> ORGANISM: Artificial Sequence
<220> FEATURE:
<223> OTHER INFORMATION: Linear GFP reverse primer

<400> SEQUENCE: 2
cttgtacagc tcgtccatgc                                              20

<210> SEQ ID NO 3
<211> LENGTH: 25
<212> TYPE: DNA
<213> ORGANISM: Artificial Sequence
<220> FEATURE:
<223> OTHER INFORMATION: Circular GFP forward primer (selfsplicing)

<400> SEQUENCE: 3
gataagcttg ccacctcagt agatg                                        25

<210> SEQ ID NO 4
<211> LENGTH: 22
<212> TYPE: DNA
<213> ORGANISM: Artificial Sequence
<220> FEATURE:
<223> OTHER INFORMATION: Circular GFP reverse primer (selfsplicing)

<400> SEQUENCE: 4
atccatcaca ctggcatatg ac                                           22

<210> SEQ ID NO 5
<211> LENGTH: 21
<212> TYPE: DNA
<213> ORGANISM: Artificial Sequence
<220> FEATURE:
<223> OTHER INFORMATION: Circular GFP forward primer (ZKSCAN)

<400> SEQUENCE: 5
gctgaccctg aagttcatct g                                            21

<210> SEQ ID NO 6
<211> LENGTH: 21
<212> TYPE: DNA
<213> ORGANISM: Artificial Sequence
<220> FEATURE:
<223> OTHER INFORMATION: Circular GFP reverse primer (ZKSCAN)

<400> SEQUENCE: 6
cttgtagttg ccgtcgtcct t                                            21

<210> SEQ ID NO 7
<211> LENGTH: 20
<212> TYPE: DNA
<213> ORGANISM: Artificial Sequence
<220> FEATURE:
<223> OTHER INFORMATION: RIG-I forward primer

<400> SEQUENCE: 7
tgtgggcaat gtcatcaaaa                                              20

<210> SEQ ID NO 8
<211> LENGTH: 21
```

```
<212> TYPE: DNA
<213> ORGANISM: Artificial Sequence
<220> FEATURE:
<223> OTHER INFORMATION: RIG-I reverse primer

<400> SEQUENCE: 8
gaagcacttg ctacctcttg c                                              21

<210> SEQ ID NO 9
<211> LENGTH: 19
<212> TYPE: DNA
<213> ORGANISM: Artificial Sequence
<220> FEATURE:
<223> OTHER INFORMATION: MDA5 forward primer

<400> SEQUENCE: 9
ggcaccatgg gaagtgatt                                                 19

<210> SEQ ID NO 10
<211> LENGTH: 20
<212> TYPE: DNA
<213> ORGANISM: Artificial Sequence
<220> FEATURE:
<223> OTHER INFORMATION: MDA5 reverse primer

<400> SEQUENCE: 10
atttggtaag gcctgagctg                                                20

<210> SEQ ID NO 11
<211> LENGTH: 21
<212> TYPE: DNA
<213> ORGANISM: Artificial Sequence
<220> FEATURE:
<223> OTHER INFORMATION: OAS forward primer

<400> SEQUENCE: 11
gctcctaccc tgtgtgtgtg t                                              21

<210> SEQ ID NO 12
<211> LENGTH: 21
<212> TYPE: DNA
<213> ORGANISM: Artificial Sequence
<220> FEATURE:
<223> OTHER INFORMATION: OAS reverse primer

<400> SEQUENCE: 12
tggtgagagt actgaggaag a                                              21

<210> SEQ ID NO 13
<211> LENGTH: 20
<212> TYPE: DNA
<213> ORGANISM: Artificial Sequence
<220> FEATURE:
<223> OTHER INFORMATION: OASL forward primer

<400> SEQUENCE: 13
agggtacaga tgggacatcg                                                20

<210> SEQ ID NO 14
<211> LENGTH: 20
<212> TYPE: DNA
<213> ORGANISM: Artificial Sequence
<220> FEATURE:
<223> OTHER INFORMATION: OASL reverse primer

<400> SEQUENCE: 14
```
aagggttcac gatgaggttg                                          20

<210> SEQ ID NO 15
<211> LENGTH: 20
<212> TYPE: DNA
<213> ORGANISM: Artificial Sequence
<220> FEATURE:
<223> OTHER INFORMATION: PKR forward primer

<400> SEQUENCE: 15
tcgctggtat cactcgtctg                                          20

<210> SEQ ID NO 16
<211> LENGTH: 20
<212> TYPE: DNA
<213> ORGANISM: Artificial Sequence
<220> FEATURE:
<223> OTHER INFORMATION: PKR reverse primer

<400> SEQUENCE: 16
gattctgaag accgccagag                                          20

<210> SEQ ID NO 17
<211> LENGTH: 20
<212> TYPE: DNA
<213> ORGANISM: Artificial Sequence
<220> FEATURE:
<223> OTHER INFORMATION: INFb forward primer

<400> SEQUENCE: 17
ctctcctgtt gtgcttctcc                                          20

<210> SEQ ID NO 18
<211> LENGTH: 22
<212> TYPE: DNA
<213> ORGANISM: Artificial Sequence
<220> FEATURE:
<223> OTHER INFORMATION: INFb reverse primer

<400> SEQUENCE: 18
gtcaaagttc atcctgtcct tg                                       22

<210> SEQ ID NO 19
<211> LENGTH: 27
<212> TYPE: DNA
<213> ORGANISM: Artificial Sequence
<220> FEATURE:
<223> OTHER INFORMATION: DDX58 oligonucleotide 1

<400> SEQUENCE: 19
acaccggatt tctgctgttc atacacg                                  27

<210> SEQ ID NO 20
<211> LENGTH: 27
<212> TYPE: DNA
<213> ORGANISM: Artificial Sequence
<220> FEATURE:
<223> OTHER INFORMATION: DDX58 oligonucleotide 2

<400> SEQUENCE: 20
aaaacgtgta tgaacagcag aaatccg                                  27

<210> SEQ ID NO 21
<211> LENGTH: 20
<212> TYPE: DNA
<213> ORGANISM: Artificial Sequence

```
<220> FEATURE:
<223> OTHER INFORMATION: DDX58

<400> SEQUENCE: 21
gatttctgct gttcatacac                                              20

<210> SEQ ID NO 22
<211> LENGTH: 20
<212> TYPE: DNA
<213> ORGANISM: Artificial Sequence
<220> FEATURE:
<223> OTHER INFORMATION: DDX58 forward primer

<400> SEQUENCE: 22
ggctgttggc atgctactta                                              20

<210> SEQ ID NO 23
<211> LENGTH: 20
<212> TYPE: DNA
<213> ORGANISM: Artificial Sequence
<220> FEATURE:
<223> OTHER INFORMATION: DDX58 reverse primer

<400> SEQUENCE: 23
ccttagcaca gagcctgaca                                              20

<210> SEQ ID NO 24
<211> LENGTH: 24
<212> TYPE: DNA
<213> ORGANISM: Artificial Sequence
<220> FEATURE:
<223> OTHER INFORMATION: DDX58 nested forward primer

<400> SEQUENCE: 24
tcagctcagt ggtattagaa gagc                                         24

<210> SEQ ID NO 25
<211> LENGTH: 20
<212> TYPE: DNA
<213> ORGANISM: Artificial Sequence
<220> FEATURE:
<223> OTHER INFORMATION: DDX58 nested reverse primer

<400> SEQUENCE: 25
tgtgccacgt aaacatcaaa                                              20

<210> SEQ ID NO 26
<211> LENGTH: 21
<212> TYPE: DNA
<213> ORGANISM: Artificial Sequence
<220> FEATURE:
<223> OTHER INFORMATION: forward primer

<400> SEQUENCE: 26
ggggaaagtt gtcttttttg c                                            21

<210> SEQ ID NO 27
<211> LENGTH: 26
<212> TYPE: DNA
<213> ORGANISM: Artificial Sequence
<220> FEATURE:
<223> OTHER INFORMATION: reverse primer

<400> SEQUENCE: 27
tacctaccca tgtctttcaa agtatt                                       26
```

```
<210> SEQ ID NO 28
<211> LENGTH: 20
<212> TYPE: DNA
<213> ORGANISM: Artificial Sequence
<220> FEATURE:
<223> OTHER INFORMATION: probe 1

<400> SEQUENCE: 28
gggaggtttt atgatgtgtt                                                   20

<210> SEQ ID NO 29
<211> LENGTH: 20
<212> TYPE: DNA
<213> ORGANISM: Artificial Sequence
<220> FEATURE:
<223> OTHER INFORMATION: probe 2

<400> SEQUENCE: 29
caggaactga cttgatccaa                                                   20

<210> SEQ ID NO 30
<211> LENGTH: 20
<212> TYPE: DNA
<213> ORGANISM: Artificial Sequence
<220> FEATURE:
<223> OTHER INFORMATION: probe 3

<400> SEQUENCE: 30
ctattacgat accatccttc                                                   20

<210> SEQ ID NO 31
<211> LENGTH: 20
<212> TYPE: DNA
<213> ORGANISM: Artificial Sequence
<220> FEATURE:
<223> OTHER INFORMATION: probe 4

<400> SEQUENCE: 31
gaatatctct gggtctggag                                                   20

<210> SEQ ID NO 32
<211> LENGTH: 20
<212> TYPE: DNA
<213> ORGANISM: Artificial Sequence
<220> FEATURE:
<223> OTHER INFORMATION: probe 5

<400> SEQUENCE: 32
ccactgatga caaagttcct                                                   20

<210> SEQ ID NO 33
<211> LENGTH: 20
<212> TYPE: DNA
<213> ORGANISM: Artificial Sequence
<220> FEATURE:
<223> OTHER INFORMATION: probe 6

<400> SEQUENCE: 33
cagaagctcc aggatctgtt                                                   20

<210> SEQ ID NO 34
<211> LENGTH: 20
<212> TYPE: DNA
<213> ORGANISM: Artificial Sequence
<220> FEATURE:
<223> OTHER INFORMATION: probe 7
```

<400> SEQUENCE: 34
atcaagctcc aagtcttcta         20

<210> SEQ ID NO 35
<211> LENGTH: 20
<212> TYPE: DNA
<213> ORGANISM: Artificial Sequence
<220> FEATURE:
<223> OTHER INFORMATION: probe 8

<400> SEQUENCE: 35
gaaggtcaaa gctcgaggac         20

<210> SEQ ID NO 36
<211> LENGTH: 1516
<212> TYPE: DNA
<213> ORGANISM: Artificial Sequence
<220> FEATURE:
<223> OTHER INFORMATION: circular RNA

<400> SEQUENCE: 36

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagaag    720
cttagccatg gcttcccgcc ggaggtggag gagcaggatg atggcacgct gcccatgtct    780
tgtgcccagg agagcgggat ggaccgtcac cctgcagcct gtgcttctgc taggatcaat    840
gtgtagatct gcagaattcg cccttcatct agggcggcca attccgcccc tctccctccc    900
cccccctaa cgttactggc cgaagccgct tggaataagg ccggtgtgcg tttgtctata    960
tgtgattttc caccatattg ccgtcttttg gcaatgtgag ggcccggaaa cctggccctg   1020
tcttcttgac gagcattcct aggggtcttt ccctctcgc caaaggaatg caaggtctgt   1080
tgaatgtcgt gaaggaagca gttcctctgg aagcttcttg aagacaaaca acgtctgtag   1140
cgacccttg caggcagcgg aaccccccac ctggcgacag gtgcctctgc ggccaaaagc   1200
cacgtgtata agatacacct gcaaaggcgg cacaaccca gtgccacgtt gtgagttgga   1260
tagttgtgga aagagtcaaa tggctctcct caagcgtatt caacaagggg ctgaaggatg   1320
cccagaaggt accccattgt atgggatctg atctggggcc tcggtgcaca tgctttacat   1380
gtgtttagtc gaggttaaaa aaacgtctag gccccccgaa ccacggggac gtggttttcc   1440
tttgaaaaac acgatgataa gcttgccacc tcagtagatg ttttcttggg tctaccgttt   1500
aatattgcgt catatc                                                  1516
```

```
<210> SEQ ID NO 37
<211> LENGTH: 8
<212> TYPE: PRT
<213> ORGANISM: Mus musculus

<400> SEQUENCE: 37

Ser Ile Ile Asn Phe Glu Lys Leu
1               5

<210> SEQ ID NO 38
<211> LENGTH: 50
<212> TYPE: DNA
<213> ORGANISM: Artificial sequence
<220> FEATURE:
<223> OTHER INFORMATION: synthetic

<400> SEQUENCE: 38
cctcagtaga tgttttcttg ggtctaccgt ttaatattgc gtcatatgcc          50
```

CIRCULAR RNAS AND THEIR USE IN IMMUNOMODULATION

This application is a U.S. 371 national phase entry of International Patent Application No. PCT/US2017/037702, filed Jun. 15, 2017, which claims priority to provisional patent application No. 62/352,471, filed Jun. 20, 2016, which is are herein incorporated by reference in its entirety their entireties.

STATEMENT REGARDING FEDERALLY SPONSORED RESEARCH OR DEVELOPMENT

This invention was made with Government support under contracts HG007735 and HG004361 awarded by the National Institutes of Health. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,000 byte ASCII (Text) file named "35308-252_ST25.txt." created on Sep. 1, 2021.

TECHNICAL FIELD

The present disclosure pertains generally to immunomodulation using circular RNAs. In particular, the disclosure relates to methods of modifying an RNA by circularization and the use of circular RNAs generated with exogenous introns to stimulate an innate immune response or circular RNAs generated with endogenous introns to prevent immune recognition of foreign RNA.

BACKGROUND

Circular RNAs (circRNAs) are single-stranded RNAs that are joined head to tail. Initially discovered in pathogenic genomes such as hepatitis D virus (HDV) and plant viroids (Kos, A., Dijkema, R., Amberg, A. C., van der Meide, P. H. & Schellekens, H. The hepatitis delta ([delta]) virus possesses a circular RNA. *Nature* 323, 558-560 (1986); Sanger, H. L., Klotz, G., Riesner, D., Gross, H. J. & Kleinschmidt, A. K. Viroids are single-stranded covalently closed circular RNA molecules existing as highly base-paired rod-like structures. *Proceedings of the National Academy of Sciences of the United States of America* 73, 3852-3856 (1976)). circRNAs are recently recognized as a pervasive class of noncoding RNAs in eukaryotic cells (Salzman, J., Gawad, C., Wang, P. L., Lacayo, N. & Brown, P. O. Circular RNAs are the predominant transcript isoform from hundreds of human genes in diverse cell types. *PLoS One* 7, e30733, (2012); Memczak, S. et al. Circular RNAs are a large class of animal RNAs with regulatory potency. *Nature* 495, 333-338, (2013); Hansen, T. B. et al. Natural RNA circles function as efficient microRNA sponges. *Nature* 495, 384-388, (2013)). Generated through back splicing (Jeck, W. R. & Sharpless, N. E. Detecting and characterizing circular RNAs. *Nat Biotech* 32, 453-461, (2014)), circRNAs have been postulated to function in cell-to-cell information transfer or memory due to their extraordinary stability. Whether and how circRNAs trigger immune recognition was not previously known.

SUMMARY

The disclosure is based on the discovery that circular RNAs generated by splicing of exogenous introns stimulate innate immunity, whereas circular RNAs generated by splicing of endogenous introns prevent immune recognition of foreign RNA.

In one aspect, the disclosure includes a method of increasing immunogenicity of a target RNA by circularization. The target RNA may be circularized, for example, by backsplicing of a non-mammalian exogenous intron or splint ligation of the 5' and 3' ends of a linear RNA. In one embodiment, the circular RNA is produced from a recombinant nucleic acid encoding the target RNA to be made circular. The method comprises: a) producing a recombinant nucleic acid encoding the target RNA to be made circular, wherein the recombinant nucleic acid comprises in 5' to 3' order: i) a 3' portion of an exogenous intron comprising a 3' splice site, ii) a nucleic acid sequence encoding the target RNA, and iii) a 5' portion of an exogenous intron comprising a 5' splice site; b) performing transcription, whereby RNA is produced from the recombinant nucleic acid; and c) performing splicing of the RNA, whereby the RNA circularizes to produce a circular RNA. Transcription may be performed in vitro or in vivo in a cell. In certain embodiments, the intron is a non-mammalian intron (e.g., self-splicing group I intron, self-splicing group II intron, spliceosomal intron, or tRNA intron). The circular RNA is generally more stable in the presence of exonucleases than the target RNA in linear form and also more stable inside a cell.

In certain embodiments, the recombinant nucleic acid comprises a bacterial plasmid vector or a viral vector. Exemplary viral vectors include measles virus, vesicular stomatitis virus, adenovirus, retrovirus (e.g., γ-retrovirus and lentivirus), poxvirus, adenoassociated virus, baculovirus, or herpes simplex virus vectors.

In certain embodiments, the recombinant nucleic acid further comprises a nucleic acid sequence encoding an IRES operably linked to a nucleic acid sequence encoding an immunogenic polypeptide, wherein translation of the circular RNA produced from the recombinant nucleic acid results in production of the immunogenic polypeptide. The nucleic acid sequence encoding the immunogenic polypeptide may be derived from an organism selected from, for example, a bacterium, a virus, a fungus, a protist, or a parasite.

In another embodiment, the recombinant nucleic acid further comprises an exosomal targeting sequence operably linked to the circular RNA sequence, wherein the exosomal targeting sequence directs packaging of the expressed circular RNA into exosomes.

In another aspect, the disclosure includes a host cell comprising a recombinant nucleic acid encoding a circular RNA (e.g., immunogenic or non-immunogenic). In certain embodiments, the host cell is a eukaryotic or prokaryotic cell. In another embodiment, the host cell is a mammalian, bacterial, or fungal cell. In a further embodiment, the host cell is a human cell.

In another embodiment, the host cell is an immune cell comprising a recombinant polynucleotide encoding an immunogenic circular RNA. Exemplary host immune cells include macrophages, neutrophils, dendritic cells, natural killer cells, T cells, and B cells.

In another embodiment, the host cell (e.g., bacterial, fungal, or mammalian cell) is engineered to secrete a circular RNA. For example, a recombinant nucleic acid encoding a circular RNA operably linked to an exosomal targeting sequence can be introduced into a host cell, such that the expressed circular RNA is packaged into exosomes and secreted by the host cell.

Any known method of nucleic acid delivery may be used for administration of circular RNAs (e.g., immunogenic or non-immunogenic) or recombinant nucleic acids encoding them to a subject. For example, a circular RNA, or recombinant nucleic acid encoding it, may be administered by transfection in vivo. Alternatively, the circular RNA, or recombinant nucleic acid encoding it, may be administered by transfection ex vivo, and subsequent transfer of a cell transfected with the circular RNA to the subject.

In other embodiments, a circular RNA, or recombinant nucleic acid encoding it, is delivered with a nucleic acid carrier (e.g. cationic carrier) or a nanoparticle (e.g., lipid nanoparticle, polymeric nanoparticle, nanoparticle comprising a combination of polymers and peptides, or an electrostatic complex). In yet other embodiments, the circular RNA or recombinant nucleic acid encoding it may be delivered to a subject using a recombinant virus, an exosome, liposome, or other lipid vesicle, or a cell engineered to secrete a circular RNA.

In certain embodiments, the circular RNA is conjugated to a targeting ligand (e.g., small molecule, peptide or protein) for localized delivery to a particular site (e.g., cells, tissue, or organ) in the subject. In other embodiments, the circular RNA is linked to an internalization sequence, a protein transduction domain, or a cell penetrating peptide to facilitate entry into a cell.

In another aspect, the disclosure includes a method of eliciting an innate immune response in a subject, the method comprising administering an effective amount of an immunogenic circular RNA (e.g., generated by splicing of an exogenous intron or splint ligation) to the subject. The circular RNA may activate an innate immune response, in part, by inducing expression of one or more genes involved in innate immunity, including, but not limited to, retinoic-acid-inducible gene-I (RIG-I, also known as DDX58), melanoma-differentiation-associated gene 5 (MDA5, also known as IFIH1), 2'-5' oligoadenylate synthase 1 (OAS1), OAS-like protein (OASL), and protein kinase R (PKR). In one embodiment, the immunogenic circular RNA is generated by splicing of a non-mammalian intron (e.g., self-splicing group I intron, self-splicing group II intron, spliceosomal intron, or tRNA intron). In another embodiment, the subject is a mammal.

In certain embodiments, the circular RNA is administered with a cationic carrier or a nanocarrier (e.g., a liposome, exosome, or metallic or polymeric nanoparticle loaded with the circular RNA).

In another embodiment, the disclosure includes a method of eliciting an innate immune response in a subject, the method comprising administering an effective amount of a recombinant nucleic acid encoding a circular RNA, wherein the recombinant nucleic acid comprises in 5' to 3' order: i) a 3' portion of an exogenous intron comprising a 3' splice site, ii) a nucleic acid sequence encoding an RNA exon, and iii) a 5' portion of an exogenous intron comprising a 5' splice site, wherein splicing of an RNA produced by transcription of the recombinant nucleic acid results in production of the circular RNA in the subject. In certain embodiments, the recombinant nucleic acid comprises a bacterial plasmid vector or a viral vector.

In another embodiment, the disclosure includes a method of eliciting an innate immune response in a subject, the method comprising administering an effective amount of a host cell comprising a recombinant nucleic acid encoding an immunogenic circular RNA, wherein the host cell is engineered to secrete the immunogenic circular RNA.

In another embodiment, the disclosure includes a method of eliciting an innate immune response in a subject, the method comprising administering to the subject an effective amount of an immunogenic circular RNA generated by splint ligation of a linear RNA.

In another aspect, the disclosure includes a method of enhancing an immune response in a subject, the method comprising administering an effective amount of an immunogenic circular RNA generated by splicing of an exogenous intron or splint ligation to the subject. This method may be used to treat a subject for a disease or condition in which enhancing an innate immune response is beneficial, such as, but not limited to, cancer, an infectious disease (e.g. caused by a pathogen, such as a virus, bacterium, protist, fungus, or parasite), or immunodeficiency. Accordingly, in certain embodiments, the circular RNA is administered locally at the site of a tumor or infection. In certain embodiments, the circular RNA is provided by a recombinant nucleic acid comprising in 5' to 3' order: i) a 3' portion of an exogenous intron comprising a 3' splice site, ii) a nucleic acid sequence encoding an RNA exon, and iii) a 5' portion of an exogenous intron comprising a 5' splice site, wherein splicing of an RNA produced by transcription of the recombinant nucleic acid results in production of the circular RNA in the subject. In certain embodiments, the recombinant nucleic acid comprises a bacterial plasmid vector or a viral vector.

In another embodiment, the circular RNA further comprises an IRES operably linked to an RNA sequence encoding an immunogenic polypeptide, wherein translation of the circular RNA results in production of the immunogenic polypeptide in the subject. The RNA sequence encoding the immunogenic polypeptide may be derived from an organism selected from, for example, a bacterium, a virus, a fungus, a protist, or a parasite.

In certain embodiments, the method further comprises treating the subject with one or more agents for treating an immune disorder. For example, the method may further comprises administering an antiviral agent, an antibiotic, an antifungal agent, or an antiparasitic agent to treat an infection, a chemotherapeutic agent to treat cancer, or a vaccine against an infectious disease or cancer.

In another aspect, the disclosure includes a method of treating a viral infection in a subject, the method comprising administering to the subject an effective amount of an immunogenic circular RNA. The subject may be treated either prophylactically (e.g., to prevent viral infection) or therapeutically (e.g., to treat a viral infection). In certain embodiments, the method further comprises administering a vaccine or antiviral agent.

In another aspect, the disclosure includes an immunogenic composition comprising at least one immunogen and an immunogenic circular RNA (e.g., generated by splicing of an exogenous intron or splint ligation). The immunogenic composition may further comprise a pharmaceutically acceptable excipient. In another embodiment, the immunogenic composition further comprises an adjuvant. In certain embodiments, the composition further comprises one or more other agents for treating an infection or cancer, including, but not limited to, an antiviral agent, an antibiotic, an antifungal agent, an antiparasitic agent, or a chemotherapeutic agent. In another embodiment, the composition further comprises a vaccine against cancer or an infection.

In another aspect, the disclosure includes a method of producing a polypeptide in a subject using a non-immunogenic circular RNA, the method comprising: a) providing a non-immunogenic circular RNA, wherein the non-immunogenic circular RNA is generated by splicing of an endogenous intron and comprises an IRES operably linked to an RNA sequence encoding the polypeptide; and b) introducing the non-immunogenic circular RNA into a cell of the subject, such that the circular RNA undergoes translation in the cell, whereby the polypeptide is produced in the subject. In certain embodiments, the polypeptide is therapeutic (e.g., an enzyme, hormone, neurotransmitter, cytokine, antibody, tumor suppressor, or cytotoxic agent for treating a genetic disorder, cancer, or other disease).

In certain embodiments, the non-immunogenic circular RNA is provided by a recombinant nucleic acid comprising in 5' to 3' order: i) a 3' portion of an endogenous intron comprising a 3' splice site, ii) a nucleic acid sequence encoding an RNA exon, and iii) a 5' portion of an endogenous intron comprising a 5' splice site, wherein splicing of an RNA produced by transcription of the recombinant nucleic acid results in production of the non-immunogenic circular RNA in the subject. In certain embodiments, the recombinant nucleic acid comprises a bacterial plasmid vector or a viral vector (e.g., measles virus, vesicular stomatitis virus, adenovirus, retrovirus (e.g., γ-retrovirus and lentivirus), poxvirus, adeno-associated virus, baculovirus, or herpes simplex virus vectors). The non-immunogenic circular RNA or recombinant nucleic acid encoding it may be introduced into a host cell by transfection in vivo. Alternatively, the nonimmunogenic circular RNA or recombinant nucleic acid encoding it may be introduced into a host cell by transfection ex vivo, and subsequent transfer of a cell transfected with the circular RNA or recombinant nucleic acid encoding it to the subject. In certain embodiments, the non-immunogenic circular RNA or recombinant nucleic acid encoding it is introduced into the cell using a nucleic acid carrier (e.g. cationic carrier) or a nanoparticle (e.g., lipid nanoparticle, polymeric nanoparticle, nanoparticle comprising a combination of polymers and peptides, or an electrostatic complex). In yet other embodiments, the circular RNA, or recombinant nucleic acid encoding it, is introduced into a cell using a recombinant virus, an exosome, liposome, or other lipid vesicle. In another embodiment, the host cell (e.g., mammalian cells, bacteria, or fungi) is engineered to secrete the circular RNA.

In another aspect, the disclosure includes a host cell transfected with a nonimmunogenic circular RNA. In one embodiment, the circular RNA is provided by a recombinant nucleic acid encoding the non-immunogenic circular RNA. In another embodiment, the host cell is a mammalian, bacterial, or fungal cell. In a further embodiment, the host cell is a human cell.

In yet another aspect, the disclosure provides kits comprising at least one circular RNA (e.g., immunogenic or non-immunogenic) or recombinant nucleic acid encoding a circular RNA. The kit may also include one or more transfection reagents to facilitate delivery of circular RNAs to cells. In addition, the kit may contain means for administering circular RNAs to a subject. The kit may also comprise instructions for treating a condition or disease that would benefit from an enhanced immune response due to activation of innate immunity by an immunogenic circular RNA, such as generated by splicing of an exogenous intron or splint ligation, as described herein. Alternatively or additionally, the kit may comprise instructions for treating a condition or disease that would benefit from expression of a therapeutic or immunogenic polypeptide by a circular RNA comprising an IRES operably linked to an RNA sequence encoding a therapeutic or immunogenic polypeptide.

Additional embodiments provide the use of aforementioned compositions to elicit an innate immune response in a subject or to treat or prevent a viral infection in a subject.

These and other embodiments of the subject disclosure will readily occur to those of skill in the art in view of the disclosure herein.

BRIEF DESCRIPTION OF THE FIGURES

FIG. 1A shows a schematic of circRNA synthesis by in vitro transcription from a permuted intron-exon template. FIG. 1B shows circular and linear RNA, which were treated with RNase R and analyzed by Bioanalyzer. FIG. 1C shows mutants with changed circular splicing efficiencies, which were treated with RNase R and analyzed by gel electrophoresis. FIG. 1D shows sequencing of circRNA product, which reveals a precise and uniform splice junction.

FIGS. 2A-2E show that exogenous circRNA stimulates innate immunity gene expression. FIG. 2A shows that linear and circRNA stimulate expression of specific genes. Left: scatterplot of RNA-seq result of HeLa cells transfected with linear or circRNA encoding GFP-IRES sequence. Right: Gene Ontology enrichment of genes induced by circular or linear RNA. FIG. 3B shows that circRNA stimulates expression of innate immune genes. FIG. 2C shows that circRNA transfection protects against viral infection. FIG. 2D shows the percent of all HeLa cells infected with VEEV-GFP following transfection with linear or circRNA. FIG. 2E shows the percent of HeLa cells that did not contain Cy3-labeled linear or circRNA infected with VEEV-GFP following transfection with linear or circRNA FIGS. 3A-3F shows that RIG-I is necessary and sufficient to sense exogenous circular RNA. FIG. 3A shows that RIG-I but not MDA-5 confers circRNA sensitivity in HEK293T cells. FIG. 3B shows that RIG-I is required to sense transfected circRNA in MEFs. FIG. 3C shows that RIG-I is required to sense transfected circRNA in HeLa cells. FIG. 3D shows that circRNA transfection induces RIG-I foci. FIG. 3E shows quantification of the RIG-I density. Means±SEM are shown; n z 41 cells for each condition. FIG. 3F shows quantification of the overlap fraction between RIG-I and linear or circRNA.

FIG. 4A shows that exogenous circRNA does not contain triphosphate. FIG. 4B shows that exogenous circRNA does not contain long dsRNA duplex. FIG. 4C shows that transfection of circRNA made from ligating the ends of linear RNA stimulates innate immune genes. FIG. 4D shows that circRNA samples do not contain aberrant products that stimulate immune response.

FIGS. 5A-5C show that intron sequence determines immune signaling by circRNA. FIG. 5A show HeLa cells were transfected with 500 ng of DNA plasmid programming ZKSCAN1 or td introns that produce a linear RNA or circRNA encoding GFP-IRES. FIG. 4B shows that circRNA produced from *Drosophila* laccase2 introns flanking GFP-IRES exon does not stimulate innate immune genes. FIG. 5C shows that co-expression of programmed protein-assisted and autocatalytic-splicing td circRNA still stimulates innate immune genes.

FIG. 6A shows a schematic for DNA-programmed splicing of linear or circular ZKSCAN1 or td-directed RNA with endogenous ZKSCAN1 or GFP-IRES exons. FIG. 6 shows a heatmap of associated proteins identified by ChIRP-MS for each of the spliced RNAs. FIG. 6C shows proteomic analysis of linear and circRNA ribonucleoprotein complexes. FIG. 6D shows a model of self versus non-self discrimination of mammalian circRNAs.

FIG. 9 shows a summary graph of IFN-γ secreting CD8+ T cells in mouse periphery blood after primary and secondary vaccinations.

FIG. 11 shows a comparison of results from multiple studies in mice showing that circRNA is effective at stimulating OVA-specific CD8+ cells in vivo.

DETAILED DESCRIPTION

Figure 1A:
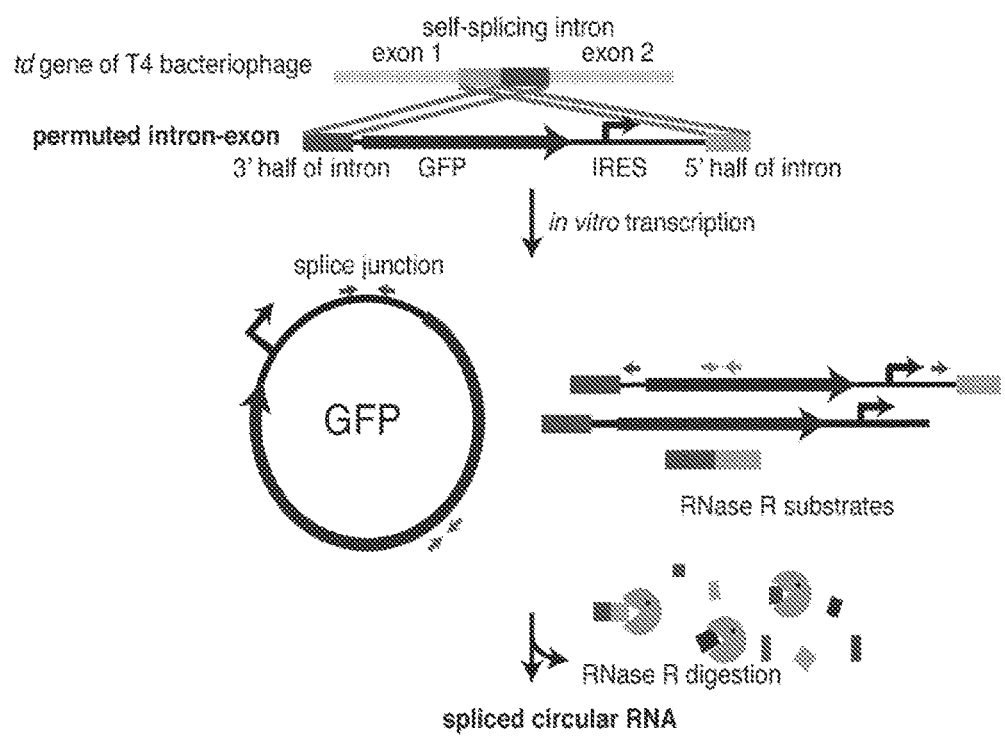
FIGS. 1A-1D show cell-free production of circRNA.

The practice of the present disclosure will employ, unless otherwise indicated, conventional methods of pharmacology, chemistry, biochemistry, recombinant DNA techniques and immunology, within the skill of the art. Such techniques are explained fully in the literature. See, e.g., Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Sambrook, et al., Molecular Cloning: A Laboratory Manual (3rd Edition, 2001); Methods In Enzymology (S. Colowick and N. Kaplan eds., Academic Press, Inc.).

All publications, patents and patent applications cited herein, whether supra or infra, are hereby incorporated by reference in their entireties.

I. DEFINITIONS

In describing the present disclosure, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a circular RNA" includes a mixture of two or more circular RNAs, and the like.

The term "about," particularly in reference to a given quantity, is meant to encompass deviations of plus or minus five percent.

"Immunogenic" means capable of inducing an innate or adaptive immunological response.

An "immunological response" or "immune response" to a circular RNA refers to the development in a subject of an innate immune response. A circular RNA may activate an innate immunological response, in part, by inducing expression of one or more genes involved in innate immunity, including, but not limited to, retinoic-acid inducible gene-I (RIG-I, also known as DDX58), melanoma-differentiation-associated gene 5 (MDA5, also known as IFIH1), 2'-5' oligoadenylate synthase 1 (OAS1), OAS-like protein (OASL), and protein kinase R (PKR).

The term "immunogenic circular RNA" refers to a circular RNA, generated by splicing of an exogenous intron, which has the ability to induce an innate immunological response in a host subject.

The term "non-immunogenic circular RNA" refers to a circular RNA, generated by splicing of an intron that is endogenous to a host subject, such that the circular RNA is treated like "self" circular RNA by the host immune system. Such a non-immunogenic circular RNA may include an exogenous exon or foreign RNA as long as the circular RNA carries the endogenous intron that confers self-identity such that the circular RNA does not provoke an innate immune response in the host subject.

The terms "peptide," "oligopeptide," and "polypeptide" refer to any compound comprising naturally occurring or synthetic amino acid polymers or amino acid-like molecules including but not limited to compounds comprising amino and/or imino molecules. No particular size is implied by use of the terms "peptide," "oligopeptide" or "polypeptide" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and 5,977,301; Nguyen et al. (2000) Chem Biol. 7(7):463-473; and Simon et al. (1992) Proc. Natl. Acad. Sci. USA 89(20):9367-9371 for descriptions of peptoids). Non-limiting lengths of peptides suitable for use in the present disclosure includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this disclosure can have a maximum length suitable for the intended application. Preferably, the polypeptide is between about 3 and 100 residues in length. Generally, one skilled in art can easily select the maximum length in view of the teachings herein. Further, peptides and polypeptides, as described herein, for example synthetic peptides, may include additional molecules such as labels or other chemical moieties.

Thus, references to polypeptides or peptides also include derivatives of the amino acid sequences of the disclosure including one or more non-naturally occurring amino acids. A first polypeptide or peptide is "derived from" a second polypeptide or peptide if it is (i) encoded by a first polynucleotide derived from a second polynucleotide encoding the second polypeptide or peptide, or (ii) displays sequence identity to the second polypeptide or peptide as described herein. Sequence (or percent) identity can be determined as described below. Preferably, derivatives exhibit at least about 50% percent identity, more preferably at least about 80%, and even more preferably between about 85% and 99% (or any value there between) to the sequence from which they were derived. Such derivatives can include post expression modifications of the polypeptide or peptide, for example, glycosylation, acetylation, phosphorylation, and the like.

Amino acid derivatives can also include modifications to the native sequence, such as deletions, additions and substitutions (generally conservative in nature), so long as the polypeptide or peptide maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: increasing affinity and/or specificity and/or facilitating cell processing. Polypeptides and peptides described herein can be made recombinantly, synthetically, or in tissue culture.

An "antigen" refers to a molecule, such as a polypeptide as defined above, containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12, or 15 amino acids. Similarly, an oligonucleotide or polynucleotide that expresses an antigen or antigenic determinant in vivo, such as in nucleic acid immunization applications, is also included in the definition of antigen herein. For purposes of the present disclosure, immunogens can be derived from any organism for which an immune response is desired, including immunogens derived from viruses, bacteria, fungi, parasites and the like.

By "fragment" is intended a polypeptide consisting of only a part of the intact full-length polypeptide sequence and structure. The fragment can include a C-terminal deletion an N-terminal deletion, and/or an internal deletion of the native polypeptide.

By "immunogenic fragment" is meant a fragment of the reference polypeptide that includes one or more epitopes and thus elicits one or more of the immunological responses described herein. An "immunogenic fragment" of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

The term "epitope" as used herein refers to a sequence of at least about 3 to 5, preferably about 5 to 10 or 15, and not more than about 500 amino acids (or any integer there between), which define a sequence that by itself or as part of a larger sequence, elicits an immunological response in the subject to which it is administered. Often, an epitope will bind to an antibody generated in response to such sequence. There is no critical upper limit to the length of the epitope, which may comprise nearly the full-length of the protein sequence, or even a fusion protein comprising two or more epitopes from the molecule in question. An epitope for use in the subject disclosure is not limited to a polypeptide having the exact sequence of the portion of the parent protein from which it is derived. For example, viral genomes are in a state of constant flux and contain several variable domains which exhibit relatively high degrees of variability between isolates.

Thus the term "epitope" encompasses sequences identical to the native sequence, as well as modifications to the native sequence, such as deletions, additions and substitutions (generally conservative in nature). Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1985) Proc. Natl. Acad. Sci. USA 82:178-182; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., Proc. Natl. Acad. Sci USA (1981) 78:3824-3828 for determining antigenicity profiles, and the Kyte-Doolittle technique, Kyte et al., J. Mol. Biol. (1982) 157:105-132 for hydropathy plots.

An "immunological response" or "immune response" to an antigen is the development in a subject of a humoral and/or a cellular immune response to an antigen present in a composition of interest. For purposes of the present disclosure, a "humoral immune response" refers to an immune response mediated by antibody molecules, while a "cellular immune response" is one mediated by T-lymphocytes and/or other white blood cells.

An "immunogenic composition" is a composition that comprises an antigenic molecule, where administration of the composition to a subject results in the development in the subject of a humoral and/or a cellular immune response to the antigenic molecule of interest. The immunogenic composition may further comprise a circular RNA that enhances the immune response through activation of innate immunity.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

"Administering" a nucleic acid, such as a circular RNA or a recombinant nucleic acid encoding a circular RNA to a cell comprises transducing, transfecting, electroporating, translocating, fusing, phagocytosing, shooting or ballistic methods, etc., i.e., any means by which a nucleic acid can be transported across a cell membrane.

The term "transfection" is used to refer to the uptake of foreign DNA or RNA (e.g., circular RNA) by a cell. A cell has been "transfected" when exogenous DNA or RNA has been introduced inside the cell membrane. A number of transfection techniques are generally known in the art. See, e.g., Green and Sambrook (2012) Molecular Cloning: A Laboratory Manual, 4th edition, Cold Spring Harbor Laboratory Press, Davis et al. (1995) Basic Methods in Molecular Biology, 2nd edition, McGraw-Hill, Chu et al. (1981) Gene 13:197, and Graham et al. (1973) Virology, 52:456. Such techniques can be used to introduce one or more exogenous DNA or RNA molecules into suitable host cells. The term refers to both stable and transient uptake of the genetic material, and includes uptake, for example, of circular RNA and nucleic acids encoding circular RNA.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

As used herein, the term "pathogen" or "parasite" or "microbe" refers to any virus or organism that spends at least part of its life cycle or reproduces within a host. Intracellular pathogens include viruses (e.g., influenza virus, respiratory syncytial virus, hepatitis virus B, hepatitis virus C, herpes virus, papilloma virus, and human immunodeficiency virus), bacteria (e.g., *Listeria*, Mycobacteria (e.g., *Mycobacterium tuberculosis, Mycobacterium leprae*), *Salmonella* (e.g., *S. typhi*), enteropathogenic *Escherichia coli* (EPEC), enterohaemorrhagic *Escherichia coli* (EHEC), *Yersinia, Shigella, Chlamydia, Chlamydophila, Staphylococcus, Legionella*), protozoa (e.g., *Plasmodium* (e.g., *P. vivax, P. falciparum, P. ovale*, and *P. malariae*), Taxoplasma, *Leishmania*), and fungi (e.g., *Aspergillus, Blastomyces, Candida*). Eukaryotic intercellular parasites include trematodes (e.g., *Schistosoma, Clonorchis*), hookworms (e.g., *Ancylostoma duodenale* and *Necator americanus*), and tape worms (e.g., *Taenia solium, T. saginata, Diphyllobothrium* spp., *Hymenolepis* spp., *Echinococcus* spp.).

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled.

The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and nonmetastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, testicular cancer, colon cancer, rectal cancer, pancreatic cancer, gastrointestinal cancer, hepatic cancer, endometrial cancer, leukemia, lymphoma, adrenal cancer, thyroid cancer, pituitary cancer, adrenocortical cancer, renal cancer, brain cancer (e.g., glioblastoma and astrocytoma), skin cancer (e.g., basal-cell cancer, squamous-cell cancer, and melanoma), head cancer, neck cancer, oral cavity cancer, tongue cancer, and esophageal cancer.

An "effective amount" of a composition comprising an immunogenic circular RNA (e.g., generated by splicing of an exogenous intron or splint ligation) or a recombinant nucleic acid encoding such a circular RNA is an amount sufficient to effect beneficial or desired results, such as an amount that enhances an immune response. An effective amount can be administered in one or more administrations, applications, or dosages.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of a composition comprising a circular RNA or a recombinant nucleic acid encoding a circular RNA is intended an amount that, when administered as described herein, brings about a positive therapeutic response, such as improved recovery from an infection, cancer, or immunodeficiency. Improved recovery may include enhanced innate immunity or eradication of an infectious pathogen. Additionally, a therapeutically effective dose or amount may enhance immunity in response to vaccination. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

"Substantially purified" generally refers to isolation of a substance (e.g., compound, circular RNA, or recombinant nucleic acid) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, CA). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none;

strand=both; cutoff=60; expect=10; Matrix=BLOSUM62; Descriptions=50 sequences; sort by =HIGH SCORE; Databases=non redundant, GenBank+EMBL+DDBJ+PDB+ GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, RNA, circular RNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene or RNA of interest is cloned and then expressed in transformed organisms, as described further below.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which can be, or have been, used as recipients for a circular RNA or recombinant nucleic acid encoding a circular RNA, or a recombinant vector or other transferred DNA, and include the original progeny of the original cell which has been transfected.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a circular RNA, recombinant nucleic acid encoding a circular RNA, or mRNA from a DNA or RNA template and can further include translation of a protein from a mRNA template or a circular RNA comprising an IRES sequence. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Purified polynucleotide" refers to a polynucleotide of interest or fragment thereof, which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Gene transfer" or "gene delivery" refers to methods or systems for reliably inserting DNA or RNA (e.g., circular RNA) of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

"Treatment," as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the disclosure find use in experimental animals, in veterinary application, and in the development of animal models for disease, including, but not limited to, rodents including mice, rats, and hamsters; primates, and transgenic animals.

II. MODES OF CARRYING OUT THE DISCLOSURE

Before describing the present disclosure in detail, it is to be understood that this disclosure is not limited to particular formulations or process parameters as such may, of course, vary. It is also to be understood that the terminology used herein is for the purpose of describing particular embodiments of the disclosure only, and is not intended to be limiting.

Although a number of methods and materials similar or equivalent to those described herein can be used in the practice of the present disclosure, the preferred materials and methods are described herein.

The present disclosure is based on the discovery that exogenous circular RNAs potently stimulate innate immunity. The inventors showed that transfection of exogenous circular RNA into mammalian cells induced expression of innate immunity genes such as RIG-I, MDA5, OAS1, OASL, and PKR (see Example 1). In addition, transfection of mammalian cells with a recombinant DNA encoding a circular RNA, which was generated in vivo by transcription and self-splicing of an exogenous intron, was also immunogenic. The inventors further showed that use of an endogenous intron to express a foreign circRNA sequence abrogated immune activation (Example 1). Example 2 demonstrates that circular RNA induces immunity in living animals. Thus, circular RNAs generated by splicing of exogenous introns stimulate innate immunity, whereas circular RNAs generated by splicing of endogenous introns prevent immune recognition of foreign RNA.

In order to further an understanding of the disclosure, a more detailed discussion is provided below regarding circular RNAs and methods of making and using circular RNAs generated with endogenous or exogenous introns.

A. Circular RNAs

Activation of innate immunity by circular RNAs is dependent on the type of intron used to generate the circular RNA, which determines self versus nonself immune recognition. Circular RNAs generated with exogenous introns are recognized by the immune system as "nonself" and trigger an innate immune response. On the other hand, circular RNAs generated with endogenous introns are recognized by the immune system as "self" and generally do not provoke an innate immune response, even if carrying an exon comprising foreign RNA.

Accordingly, circular RNAs can be generated with either an endogenous or exogenous intron to control immunological self/nonself discrimination as desired. Numerous intron sequences from a wide variety of organisms and viruses are known and include sequences derived from genes encoding proteins, ribosomal RNA (rRNA), or transfer RNA (tRNA). Representative intron sequences are available in various databases, including the Group I Intron Sequence and Structure Database (rna.whu.edu.cn/gissd/), the Database for Bacterial Group II Introns (webapps2.ucalgary.ca/~groupii/index.html), the Database for Mobile Group II Introns (fp.ucalgary.ca/group2introns), the Yeast Intron DataBase (emb1S16 heidelberg.de/ExternalInfo/seraphin/yidb.html), the Ares Lab Yeast Intron Database (compbio.soe.ucsc.edu/yeast_introns.html), the U12 Intron Database (genome.crg.es/cgibin/u12db/u12db.cgi), and the Exon-Intron Database (bpg.utoledo.edu/~afedorov/lab/eid.html).

Circular RNAs can be produced from linear RNAs in a number of ways. In one embodiment, circular RNAs are produced from a linear RNA by backsplicing of a downstream 5' splice site (splice donor) to an upstream 3' splice site (splice acceptor). Circular RNAs can be generated in this manner by any nonmammalian splicing method. For example, linear RNAs containing various types of introns, including self-splicing group I introns, self-splicing group II introns, spliceosomal introns, and tRNA introns can be circularized. In particular, group I and group II introns have the advantage that they can be readily used for production of circular RNAs in vitro as well as in vivo because of their ability to undergo self-splicing due to their autocatalytic ribozyme activity.

Alternatively, circular RNAs can be produced in vitro from a linear RNA by chemical or enzymatic ligation of the 5' and 3' ends of the RNA. Chemical ligation can be performed, for example, using cyanogen bromide (BrCN) or ethyl-3-(3'-dimethylaminopropyl) carbodiimide (EDC) for activation of a nucleotide phosphomonoester group to allow phosphodiester bond formation. See e.g., Sokolova (1988) FEBS Lett 232:153-155; Dolinnaya et al. (1991) Nucleic Acids Res., 19:3067-3072; Fedorova (1996) Nucleosides Nucleotides Nucleic Acids 15:1137-1147; herein incorporated by reference. Alternatively, enzymatic ligation can be used to circularize RNA. Exemplary ligases that can be used include T4 DNA ligase (T4 Dnl), T4 RNA ligase 1 (T4 Rnl 1), and T4 RNA ligase 2 (T4 Rnl 2).

Additionally, splint ligation using an oligonucleotide splint that hybridizes with the two ends of a linear RNA can be used to bring the ends of the linear RNA together for ligation. Hybridization of the splint, which can be either a deoxyribooligonucleotide or a ribooligonucleotide, orientates the 5'-phophate and 3'-OH of the RNA ends for ligation. Subsequent ligation can be performed using either chemical or enzymatic techniques, as described above. Enzymatic ligation can be performed, for example, with T4 DNA ligase (DNA splint required), T4 RNA ligase 1 (RNA splint required) or T4 RNA ligase 2 (DNA or RNA splint). Chemical ligation, such as with BrCN or EDC, in some cases is more efficient than enzymatic ligation if the structure of the hybridized splint-RNA complex interferes with enzymatic activity. See, e.g., Dolinnaya et al. (1993) Nucleic Acids Res 21(23):5403-5407; Petkovic et al. (2015) Nucleic Acids Res 43(4):2454-2465; herein incorporated by reference in their entireties.

A circular RNA may further comprise an internal ribosome entry site (IRES) operably linked to an RNA sequence encoding a polypeptide. Inclusion of an IRES permits the translation of one or more open reading frames from a circular RNA. The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20:102-110; Kobayashi et al., BioTechniques (1996) 21:399-402; and Mosser et al., BioTechniques 1997 22 150-161).

A circular RNA construct comprising an IRES can be designed to produce any polypeptide of interest. For example, a circular RNA may comprise an IRES operably linked to an RNA sequence encoding an immunogenic polypeptide, such as from a bacterium, virus, fungus, protist, or parasite. Alternatively, a circular RNA may comprise an IRES operably linked to an RNA sequence encoding a therapeutic polypeptide such as an enzyme, hormone, neurotransmitter, cytokine, antibody, tumor suppressor, or cytotoxic agent for treating a genetic disorder, cancer, or other disease.

A multitude of IRES sequences are available and include sequences derived from a wide variety of viruses, such as from leader sequences of picornaviruses such as the encephalomyocarditis virus (EMCV) UTR (Jang et al. J. Virol. (1989) 63:1651-1660), the polio leader sequence, the hepatitis A virus leader, the hepatitis C virus IRES, human rhinovirus type 2 IRES (Dobrikova et al., Proc. Natl. Acad. Sci. (2003) 100(25):15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like. A variety of nonviral IRES sequences will also find use herein, including, but not limited to IRES sequences from yeast, as well as the human angiotensin II type 1 receptor IRES (Martin et al., Mol. Cell Endocrinol. (2003) 212:51-61), fibroblast growth factor IRESs (FGF-1 IRES and FGF-2 IRES, Martineau et al. (2004) Mol. Cell. Biol. 24(17):7622-7635), vascular endothelial growth factor IRES (Baranick et al. (2008) Proc. Natl. Acad. Sci. U.S.A. 105(12):4733-4738, Stein et al. (1998) Mol. Cell. Biol. 18(6):3112-3119, Bert et al. (2006) RNA 12(6):1074-1083), and insulin-like growth factor 2 IRES (Pedersen et al. (2002) Biochem. J. 363(Pt 1):37-44).

These elements are commercially available in plasmids sold, e.g., by Clontech (Mountain View, CA), Invivogen (San Diego, CA), Addgene (Cambridge, MA) and GeneCopoeia (Rockville, MD.). See also IRESite: The database of experimentally verified IRES structures (iresite.org).

Polynucleotides encoding the desired RNAs, polypeptides, introns, and IRESs for use with the present disclosure can be made using standard techniques of molecular biology. For example, polynucleotide sequences coding for the above-described molecules can be obtained using recombinant methods, such as by screening cDNA and genomic libraries from cells, or by deriving the polynucleotides from a vector known to include the same. Polynucleotides can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223:1299; and Jay et al., J. Biol. Chem. (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239:1534-1536), and enzymatic filling-in of gapped oligonucleotides using T4 DNA polymerase (Queen et al., Proc. Natl. Acad. Sci. USA (1989) 86:10029-10033) can be used to provide molecules for use in the subject methods.

A circular RNA can be produced by transcription in vivo or in vitro from a recombinant nucleic acid. In certain embodiments, the recombinant nucleic acid encoding the circular RNA is under transcriptional control of a promoter. A "promoter" refers to a DNA sequence recognized by the synthetic machinery of a cell, or introduced synthetic machinery, required to initiate transcription. The term promoter will be used herein to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

In certain embodiments, the recombinant nucleic acid encoding the circular RNA comprises a vector. A "vector" is a composition of matter which can be used to deliver a nucleic acid of interest to the interior of a cell. Vectors include, but are not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the disclosure in a general, illustrative sense, and are not intended to limit the disclosure.

In one embodiment, an expression vector for expressing a circular RNA comprises a promoter "operably linked" to a polynucleotide encoding the circular RNA. The phrase "operably linked" or "under transcriptional control" as used herein means that the promoter is in the correct location and orientation in relation to a polynucleotide to control the initiation of transcription by RNA polymerase and expression of the circular RNA.

In certain embodiments of the disclosure, cells containing nucleic acid constructs (e.g., circular RNAs or recombinant nucleic acids encoding them) of the present disclosure may be identified in vitro or in vivo by including a marker in the construct. Such markers would confer an identifiable change to the cell permitting easy identification of cells containing the construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., green fluorescent protein (GFP), EGFP, or Dronpa), or immunologic markers can also be employed. The selectable marker employed is not believed to be important, so long as it is capable of being expressed simultaneously with the nucleic acid encoding a circular RNA.

There are a number of ways in which nucleic acids (e.g., circular RNAs or recombinant nucleic acids encoding them) may be introduced into cells. In certain embodiments, a virus or engineered construct derived from a viral genome is used for delivery of a circular RNA to a cell. A number of viral based systems have been developed for transfer of nucleic acids into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference in their entireties). The ability of certain viruses to enter cells via receptor-mediated endocytosis, to integrate into host cell genomes and express viral genes stably and efficiently have made them attractive candidates for the transfer of foreign genes into mammalian cells.

For example, retroviruses provide a convenient platform for delivery of nucleic acids encoding circular RNAs. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr. Pharm. Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adenoS16-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering nucleic acids encoding circular RNAs is the enterically administered recombinant poxvirus vaccines described by Small, Jr., P. A., et al. (U.S. Pat. No. 5,676,950, issued Oct. 14, 1997, herein incorporated by reference).

Additional viral vectors which find use for delivering the nucleic acid molecules of interest include those derived from the pox family of viruses, including vaccinia virus and avian poxvirus. By way of example, vaccinia virus recombinants expressing a nucleic acid molecule of interest (e.g., circular RNA) can be constructed as follows. The DNA encoding the circular RNA sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver nucleic acid molecules of interest. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for delivery of circular RNAs. Members of the alphavirus genus, such as, but not limited to, vectors derived from the Sindbis virus (SIN), Semliki Forest virus (SFV), and Venezuelan Equine Encephalitis virus (VEE), will also find use as viral vectors for delivering the circular RNAs of the present disclosure. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of polynucleotides of interest (e.g., circular RNAs) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA. The method provides for high level, transient, cytoplasmic production of large quantities of RNA, which undergoes splicing to produce circular RNA. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of nucleic acids using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more templates. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

In order to effect expression of nucleic acid constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle. Several non-viral methods for the transfer of circular RNAs or recombinant nucleic acids encoding them into cultured mammalian cells also are contemplated by the present disclosure. These include the use of calcium phosphate precipitation, DEAEdextran, eectroporation, direct microinjection, nucleic acid-loaded liposomes or exosomes, nucleic-acid loaded nanoparticles, lipofectamine-nucleic acid complexes, cell sonication, gene bombardment using high velocity microprojectiles, and receptormediated transfection (see, e.g, Graham and Van Der Eb (1973) Virology 52:456-467; Chen and Okayama (1987) Mol. Cell Biol. 7:2745-2752; Rippe et al. (1990) Mol. Cell Biol. 10:689-695; Gopal (1985) Mol. Cell Biol. 5:1188-1190; Tur-Kaspa et al. (1986) Mol. Cell. Biol. 6:716-718; Potter et al. (1984) Proc. Natl. Acad. Sci. USA 81:7161-7165); Harland and Weintraub (1985) J. Cell Biol. 101:1094-1099); Nicolau and Sene (1982) Biochim. Biophys. Acta 721:185-190; Fraley et al. (1979) Proc. Natl. Acad. Sci. USA 76:3348-3352; Fechheimer et al. (1987) Proc Natl. Acad. Sci. USA 84:8463-8467; Yang et al. (1990) Proc. Natl. Acad. Sci. USA 87:9568-9572; Wu and Wu (1987) J. Biol. Chem. 262:4429-4432; Wu and Wu (1988) Biochemistry 27:887-892; herein incorporated by reference in their entireties). Some of these techniques may be successfully adapted for in vivo or ex vivo use.

In particular, various nanoparticulate systems can be used for delivery of circular RNA. Different types of nanocarriers include lipid, metallic, and polymeric nanoparticles, nanoparticles comprising a combination of polymers and peptides, electrostatic complexes, liposomes, exosomes, dendrimers, gelatins, and quantum dots/rods. See e.g., Liao et al. (2016) Biomater Sci. 2016 May 25 [Epub ahead of print], Mehrotra et al. (2015) IET Nanobiotechnol. 9(6):386-395, Xu et al. (2014) J Biomed Nanotechnol 10(12):3483-3507, Dahlman et al. (2014) Adv Genet 88:37-69, Aigner et al. (2016) Pharmazie 71(1):27-34, Zhou et al. (2016) Wiley Interdiscip Rev RNA 2016 May 16 [Epub ahead of print], O'Loughlin et al. (2012) Curr Gene Ther 12(4):262-274; herein incorporated by reference in their entireties.

In another embodiment, a circular RNA or recombinant nucleic encoding a circular RNA may be delivered using liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Liver Diseases, Targeted Diagnosis and Therapy Using Specific Receptors and Ligands, Wu et al. (Eds.), Marcel Dekker, NY, 87-104). Also contemplated is the use of lipofectamine-nucleic acid complexes.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al. (1989) Science 243:375-378). In other embodiments, the liposome may be complexed or employed in conjunction with nuclear non-histone chromosomal proteins (HMG-I) (Kato et al. (1991) J. Biol. Chem. 266(6): 3361-3364). In yet further embodiments, the liposome may be complexed or employed in conjunction with both HVJ and HMG-I. In that such expression constructs have been successfully employed in transfer and expression of nucleic acid in vitro and in vivo, then they are applicable for the present disclosure. Where a bacterial promoter is employed in a DNA construct, it also will be desirable to include within the liposome an appropriate bacterial polymerase.

In a further embodiment, a circular RNA may be delivered to cells using exosomes. Exosomes are membrane bound vesicles, typically 30-120 nm in size, which naturally transport cargo, including nucleic acids, between cells. Nucleic acids encapsulated in exosomes are internalized into cells by endocytosis. Exosomes, which are naturally secreted by cells, can be purified from cells, for example, using ultracentrifugation, iodixanol density gradient centrifugation, or gel filtration. Exosomes, for use in nucleic acid delivery (e.g., circular RNAs or recombinant nucleic acids encoding them), are preferably isolated from the subject to be administered the exosomes, or a matched donor or other immunologically compatible cell source. Such exosomes have the advantage that they can be used to evade immune recognition and prevent degradation of encapsulated nucleic acids. Exosomes can be loaded with circular RNAs, for example, using electroporation or other transfection techniques. For a discussion of the use of exosomes for nucleic acid delivery, see, e.g., Xitong et al. (2016) Gene. 575(2 Pt 2):377-384; Zhou et al. (2016) Wiley Interdiscip Rev RNA 2016 May 16 [Epub ahead of print], O'Loughlin et al. (2012) Curr Gene Ther 12(4):262-274, Alvarez-Erviti et al. (2011) Nat Biotechnol (4): 341-345; herein incorporated by reference in their entireties.

Alternatively, a cell can be engineered to secrete circular RNAs in exosomes by transfecting the cell with a recombinant nucleic acid encoding a circular RNA comprising an exosomal targeting sequence that directs packaging of the expressed circular RNA into exosomes. RNA exosomal targeting sequences and vectors for packaging RNA into exosomes are commercially available from System Biosciences (Palo Alto, CA).

In yet another embodiment of the disclosure, the expression construct may simply consist of naked circular RNA, recombinant DNA, or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Natl. Acad. Sci. USA (1984) 81:7529-7533) successfully injected polyomavirus DNA in the form of calcium phosphate precipitates into liver and spleen of adult and newborn mice demonstrating active viral replication and acute infection. Benvenisty and Neshif (Proc. Natl. Acad. Sci. USA (1986) 83:9551-9555) also demonstrated that direct intraperitoneal injection of calcium phosphate-precipitated plasmids results in expression of the transfected genes. It is envisioned that DNA encoding a circular RNA may also be transferred in a similar manner in vivo.

In still another embodiment, a naked circular RNA or recombinant nucleic encoding a circular RNA may be transferred into cells by particle bombardment. This method depends on the ability to accelerate nucleic acid-coated microprojectiles to a high velocity allowing them to pierce cell membranes and enter cells without killing them (Klein et al. (1987) Nature 327:70-73). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

Other expression constructs which can be employed to deliver a circular RNA into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993) Adv. Drug Delivery Rev. 12:159-167).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin (see, e.g., Wu and Wu (1987), supra; Wagner et al. (1990) Proc. Natl. Acad. Sci. USA 87(9):3410-3414). Recently, a synthetic neoglycoprotein, which recognizes the same receptor as ASOR, has been used as a gene delivery vehicle (Ferkol et al. (1993) FASEB J. 7:1081-1091; Perales et al. (1994) Proc. Natl. Acad. Sci. USA 91(9):4086-4090), and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (Methods Enzymol. (1987) 149:157-176) employed lactosyl-ceramide, a galactose-terminal asialganglioside, incorporated into liposomes and observed an increase in the uptake of the insulin gene by hepatocytes. Thus, it is feasible that a nucleic acid encoding a circular RNA also may be specifically delivered into a cell by any number of receptor-ligand systems with or without liposomes. Also, antibodies to surface antigens on particular cells can similarly be used as targeting moieties.

In a particular example, a circular RNA or recombinant nucleic acid encoding a circular RNA may be administered in combination with a cationic lipid. Examples of cationic lipids include, but are not limited to, lipofectin, DOTMA, DOPE, and DOTAP. For a discussion of various cationic lipids that can be used for delivery of nucleic acids to cells, see, e.g., Liu et al. (2003) Methods Enzymol 373:536-50, Hirko et al. (2003) Curr Med Chem. 10(14):1185-1193, Chesnoy et al. (2000) Annu Rev Biophys Biomol Struct 29:27-47, U.S. Pat. No. 7,479,573; herein incorporated by reference. The publication of WO/0071096, which is specifically incorporated by reference, describes different formulations, such as a DOTAP:cholesterol or cholesterol derivative formulations that can effectively be used for nucleic acid delivery. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 55,844, 107, 5,877,302, 6,008,336, 6,077,835, 5,972,901, 6,200,801, and 5,972,900, which are incorporated by reference for those aspects.

In certain embodiments, transfer of circular RNAs or recombinant nucleic acids encoding them may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Circular RNAs can be conjugated to a targeting ligand or targeting agent (e.g., small molecule, peptide, or protein) to direct delivery to particular locations in a subject, such as specific organs, tissues, or cells. Targeting agents can be chosen that recognize tissue-specific markers, organ-specific markers, or disease-specific markers (e.g., cell surface protein or epitope associated with a specific tissue, organ, or disease state, or a tumor marker). Exemplary targeting agents include an RGD peptide, an NGR peptide, folate, transferrin, GM-CSF, galactosamine, growth factor receptors (e.g. IGF-1R, MET, EGFR), antibodies and antibody fragments including anti-VEGFR, anti-ERBB2, antitenascin, anti-CEA, anti-MUC1, anti-TAG72, mutagenic bacterial strain markers, and fatty acids.

In addition, a circular RNA can be linked to an internalization sequence, a protein transduction domain, or a cell-penetrating peptide to facilitate entry into a cell. Cell penetrating peptides that can be used in the practice of the disclosure include, but are not limited to, human immunodeficiency virus (HIV) trans-activator of transcription (TAT), penetratin, transportan, octaarginine, nonaarginine, antennapedia, TP10, Buforin II, MAP (model amphipathic peptide), K-FGF, Ku70, mellittin, pVEC, Pep-1, SynB1, Pep-7, CADY, GALA, pHLIP, KALA, R7W, and HN-1.

Circular RNAs or recombinant nucleic acids encoding them may also comprise a detectable label in order to determine cellular uptake efficiency or visualize localization. Detectable labels suitable for use in the present disclosure include any composition detectable by spectroscopic, photochemical, biochemical, immunochemical, electrical, optical, or chemical means. Useful labels in the present disclosure include biotin or other streptavidin-binding proteins for staining with a labeled streptavidin conjugate, magnetic beads (e.g., Dynabeads), fluorescent dyes (e.g., fluorescein, rhodamine, coumarin, or cyanine derivatives), green fluorescent protein, and the like (see, e.g., Molecular Probes, Eugene, Oreg., USA), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. In addition, magnetic resonance imaging (MRI) contrast agents (e.g., gadodiamide, gadobenic acid, gadopentetic acid, gadoteridol, gadofosveset, gadoversetamide, gadoxetic acid), and computed tomography (CT) contrast agents (e.g., Diatrizoic acid, Metrizoic acid, Iodamide, Iotalamic acid, Ioxitalamic acid, Ioglicic acid, Acetrizoic acid, Iocarmic acid, Methiodal, Diodone, Metrizamide, Iohexol, Ioxaglic acid, Iopamidol, Iopromide, Iotrolan, Ioversol, Iopentol, Iodixanol, Iomeprol, Iobitridol, Ioxilan, Iodoxamic acid, Iotroxic acid, Ioglycamic acid, Adipiodone, Iobenzamic acid, Iopanoic acid, Iocetamic acid, Sodium Iopodate, Tyropanoic acid, Calcium iopodate) are useful as labels in medical imaging. Patents teaching the use of such labels include U.S. Pat. Nos. 3,817,837; 3,850,752; 3,939,350; 3,996,345; 4,277,437; 4,275,149; 4,366,241; 5,798,092; 5,695,739; 5,733,528; and 5,888,576.

B. Enhancing Innate Immunity with Circular RNAs

Immunogenic circular RNAs (e.g., generated by splicing of exogenous introns or splint ligation) can be used to elicit an innate immune response in a subject. The circular RNA may activate an innate immune response, in part, by inducing expression of one or more genes involved in innate immunity, including, but not limited to, retinoic-acid S16-inducible gene-I (RIG-I, also known as DDX58), melanoma-differentiation-associated gene 5 (MDA5, also known as IFIH1), 2'-5' oligoadenylate synthase 1 (OAS1), OAS-like protein (OASL), and protein kinase R (PKR).

The methods of the disclosure are useful for treating various immune conditions and disorders. For example, an immunogenic circular RNA can be used for treating infectious diseases, such as caused by a virus or cellular pathogen, by increasing an immune response to a cancerous cell or tumor in an individual, or enhancing an immuneresponse in an individual who is immunodeficient or immunocompromised.

In some embodiments, an immunogenic circular RNA is used to enhance an innate immune response for treating: (a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia), a picornavirus (e.g., rhinovirus or enterovirus), an orthomyxovirus (e.g., influenza virus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as human immunodeficiency virus (HIV)); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, and *Bordetella*; (c) other infectious diseases, such as, but not limited to *Chlamydia* infection, fungal diseases including but not limited to candidiasis, aspergillosis, blastomycosis, histoplasmosis, cryptococcal meningitis, and parasitic diseases including but not limited to malaria, *Pneumocystis carinii* pneumonia, leishmaniasis, cryptosporidiosis, toxoplasmosis, and trypanosome infection; (d) cancer, including squamous cell carcinoma, adenocarcinoma, adenosquamous carcinoma, anaplastic carcinoma, large cell carcinoma, or small cell carcinoma, including cancer in various tissues and organs, such as, but not limited to, breast cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer; and (e) immunodeficiency, including primary and secondary immunodeficiencies, such as, but not limited to, immunodeficiency caused by acquired immune deficiency syndrome (AIDS), multiple myeloma, chronic lymphoid leukemia, lymphoma, chronic granulomatous disease, severe combined immunodeficiency (SCID), X-linked agammaglobulinemia, thymoma with immunodeficiency, common variable immunodeficiency (CVID), Wiskott-Aldrich syndrome, hepatic venoocclusive disease with immunodeficiency (VODI), sickle-cell anemia, bone marrow and other transplantation, splenectomy, cancer chemotherapy, disease-modifying antirheumatic drugs, glucocorticoid therapy, immunosuppressive drugs, and environmental exposure to toxins. In addition, an immunogenic circular RNA may be used to enhance the immune response to antibiotic-resistant bacteria and for treating sepsis or food poisoning.

As mentioned above, circular RNAs may further comprise an IRES to allow expression of a polypeptide. Thus, an immunogenic circular RNA that enhances innate immunity may further include an IRES operably linked to an RNA sequence encoding an immunogenic polypeptide that elicits an adaptive immune response. Alternatively or additionally, an immunogenic circular RNA (e.g., with or without an IRES operably linked to an RNA sequence encoding an immunogenic polypeptide) may be administered in combination with an immunogen or vaccine to augment the immune response to a cellular pathogen or cancerous cells. Immunogens can include antigens of viral, bacterial, mycobacterial, fungal, protistic, parasitic, or cancerous or tumorigenic origin.

Non-limiting examples of viral pathogens that affect humans and/or nonhuman vertebrates from which immunogens can be derived, or which can be provided in attenuated or inactivated form include retroviruses, RNA viruses and DNA viruses. The group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, HIV-2, SIV, Visna virus, feline immunodeficiency virus (FIV), and equine infectious anemia virus (EIAV). The T-cell leukemia viruses include HTLV-1, HTLV-II, simian Tcell leukemia virus (STLV), and bovine leukemia virus (BLV). The foamy viruses include human foamy virus (HFV), simian foamy virus (SFV) and bovine foamy virus (BFV).

Examples of other RNA viruses from which immunogens can be derived include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'NyongS16-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (*Influenza* virus type A, many human subtypes); Swine influenza virus, and Avian and Equine *Influenza* viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (CrimeanS16-Congo hemorrhagic fever virus, Nairobi sheep disease virus), and the genus *Uukuvirus* (Uukuniemi and related viruses); the family Orthomyxoviridae, including the genus *Influenza* virus (*Influenza* virus type A, many human subtypes); Swine influenza virus, and Avian and Equine *Influenza* viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including the SARS virus, Infectious Bronchitis Virus (IBV), Mouse Hepatitis virus, Human enteric corona virus, and Feline infectious peritonitis (Feline coronavirus).

Illustrative DNA viruses from which immunogens can be derived include, but are not limited to: the family Poxviridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-herpesviruses (Herpes Simplex virus Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the beta-herpesvirises (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

Non-limiting examples of bacterial pathogens from which immunogens can be derived include both gram negative and gram positive bacteria. Gram positive bacteria include, but are not limited to *Pasteurella* species, Staphylococci species, and *Streptococcus* species. Gram negative bacteria include, but are not limited to, *Escherichia coli, Pseudomonas species*, and *Salmonella* species. Specific examples of infectious bacteria include but are not limited to: *Helicobacter pylori, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus infuenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelli*.

Examples of infectious fungi from which immunogens can be derived include: *Cryptococcus neoformans, Histoplasma capsulatum, Coccidioides immitis, Blastomyces dermatitidis, Chlamydia trachomatis*, and *Candida albicans*. Examples of infectious parasites include *Plasmodium* such as *Plasmodium falciparum, Plasmodium malariae, Plasmodium ovale*, and *Plasmodium vivax*. Other infectious organisms (i.e. protists) include *Toxoplasma gondii*.

Other medically relevant microorganisms have been described extensively in the literature. See, e.g. C. G. A Thomas, Medical Microbiology, Bailliere Tindall, Great Britain 1983, the entire contents of which is hereby incorporated by reference. Treatment of primates, more particularly humans is of interest, but other mammals may also benefit from treatment, particularly domestic animals such as equine, bovine, ovine, feline, canine, murine, lagomorpha, and the like. It is readily apparent that a wide variety of immunogens for both human and nonhuman organisms can be combined with circular RNAs. These immunogens can be provided as attenuated, inactivated or subunit vaccine compositions. Additionally, the immunogens can be provided in nucleic acid constructs for DNA immunization. Techniques for preparing DNA immunogens are well known in the art and described in, e.g., U.S. Pat. Nos. 5,399,346, 5,580,859, 5,589,466, incorporated by reference herein in their entireties.

C. Pharmaceutical Compositions

The present disclosure also encompasses pharmaceutical compositions comprising circular RNAs or recombinant nucleic acids encoding circular RNAs and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for circular RNAs or recombinant nucleic acids encoding circular RNAs described herein. Commercially available fat emulsions that are suitable for delivering the nucleic acids of the disclosure to tissues include Intralipid, Liposyn, Liposyn II, Liposyn III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO 03/093449, which are herein incorporated by reference in their entireties.

In particular, cationic liposome formulations comprising lipofectamine can be used for delivery. Lipofectamine may be formulated with a neutral co-lipid or helper lipid. See e.g., U.S. Pat. No. 7,479,573, Dalby et al. (2004) Science Direct, Methods 33:95-103, Hawley-Nelson et al. (1993) Focus 15:73-79; herein incorporated by reference in their entireties.

One will generally desire to employ appropriate salts and buffers to render delivery vehicles stable and allow for uptake by target cells. Buffers also will be employed when recombinant cells (e.g., transfected ex vivo with a circular RNA or recombinant nucleic acid encoding a circular RNA) are introduced into a patient. Aqueous compositions of the present disclosure comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the nucleic acids of the compositions.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The pharmaceutical preparations herein can also be housed in a syringe, an implantation device, or the like, depending upon the intended mode of delivery and use. Preferably, the compositions comprising circular RNAs or recombinant nucleic acids encoding them, prepared as described herein, are in unit dosage form, meaning an amount of a composition appropriate for a single dose, in a premeasured or pre-packaged form.

The compositions herein may optionally include one or more additional agents, such as other drugs for treating immune diseases and conditions, or other medications used to treat a subject for a condition or disease. For example, compositions comprising immunogenic circular RNAs (e.g., generated by splicing of exogenous introns or splint ligation), or recombinant nucleic acids encoding them, may also contain one or more other drugs for treating cancer, an infection, or immunodeficiency, such as, but not limited to, chemotherapeutic agents, such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon; antimicrobial agents, including antiseptics, antibiotics, antifungal agents, antiviral agents, antiparasitic agents; and vaccines.

Alternatively, such agents may be contained in a separate composition from the composition comprising the circular RNAs or recombinant nucleic acids encoding them and co-administered concurrently, before, or after the composition comprising the circular RNAs or recombinant nucleic acids encoding them.

D. Administration

At least one therapeutically effective cycle of treatment with an immunogenic circular RNA is administered to a subject for treatment of an immune disease or condition. By "therapeutically effective dose or amount" of a composition comprising an immunogenic circular RNA (e.g., generated by splicing of exogenous introns or splint ligation) is intended an amount that, when administered as described herein, brings about a positive therapeutic response, such as improved recovery from cancer, an infection, or immunodeficiency. Improved recovery may include enhanced immunity or eradication of an infectious pathogen. Additionally, a therapeutically effective dose or amount may have anti-tumor activity.

In certain embodiments, multiple therapeutically effective doses of compositions comprising circular RNAs or recombinant nucleic acids encoding them and/or one or more other therapeutic agents, such as other drugs for treating immune diseases or conditions, or other medications will be administered. The compositions of the present disclosure are typically, although not necessarily, administered via injection (subcutaneously, intravenously, intra-arterially, or intramuscularly), by infusion, or locally. Additional modes of administration are also contemplated, such as intraperitoneal, intrathecal, intratumor, intralymphatic, intravascular, intralesion, transdermal, and so forth. In some embodiments, the pharmaceutical composition comprising a circular RNA or a recombinant nucleic acid encoding a circular RNA is administered locally, for example, to the site of an infected, cancerous, or inflamed region needing treatment. The pharmaceutical compositions comprising circular RNAs (or recombinant nucleic acids encoding them) and other agents may be administered using the same or different routes of administration in accordance with any medically acceptable method known in the art.

In another embodiment, the pharmaceutical compositions comprising circular RNAs (or recombinant nucleic acids encoding them) are administered prophylactically, e.g., to prevent infection or tumor growth. Such prophylactic uses will be of particular value for subjects with a disease or who have a genetic predisposition to developing an immune disease or condition, such as an infection (e.g., chronic granulomatous disease, osteopetrosis), immunodeficiency, inflammation, or cancer. For example, circular RNAs (or recombinant nucleic acids encoding them) may be administered to a patient who has had cancer previously and may be susceptible to relapse in order to prevent recurrence or to a person who is at high risk of developing cancer due to a genetic predisposition or environmental exposure to a carcinogen.

In another embodiment of the disclosure, the pharmaceutical compositions comprising circular RNAs (or recombinant nucleic acids encoding them) and/or other agents are in a sustained-release formulation, or a formulation that is administered using a sustained-release device. Such devices are well known in the art, and include, for example, miniature implantable pumps that can provide for delivery over time in a continuous, steady-state fashion at a variety of doses to achieve a sustained-release effect with a non-sustained-release pharmaceutical composition.

Those of ordinary skill in the art will appreciate which conditions compositions comprising circular RNAs (or recombinant nucleic acids encoding them) can effectively treat. The actual dose to be administered will vary depending upon the age, weight, and general condition of the subject as well as the severity of the condition being treated, the judgment of the health care professional, and conjugate being administered.

Therapeutically effective amounts can be determined by those skilled in the art, and are adjusted to the particular requirements of each particular case. Compositions comprising circular RNAs (or recombinant nucleic acids encoding them), prepared as described herein (again, preferably provided as part of a pharmaceutical preparation), can be administered alone or in combination with one or more other therapeutic agents for treating an immune disease or condition, including antiinflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; andimmune selective anti-inflammatory derivatives (ImSAIDs); or other drugs for treating cancer, an infection, or immunodeficiency, such as, but not limited to, chemotherapeutic agents, such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon; antimicrobial agents, including antiseptics, antibiotics, antifungal agents, antiviral agents, antiparasitic agents; and vaccines; or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Compositions comprising circular RNAs (or recombinant nucleic acids encoding them) can be administered prior to, concurrent with, or subsequent to other agents. If provided at the same time as other agents, the circular RNAs (or recombinant nucleic acids encoding them) can be provided in the same or in a different composition. Thus, circular RNAs (or recombinant nucleic acids encoding them) and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a circular RNA (or recombinant nucleic acid encoding a circular RNA) and a dose of a pharmaceutical composition comprising at least one other agent, such as a drug for treating an immune disease or condition, which in combination comprise a therapeutically effective dose, according to a particular dosing regimen. Similarly, a circular RNA (or recombinant nucleic acid encoding a circular RNA) and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

E. Kits

Any of the compositions described herein may be included in a kit. For example circular RNAs (e.g., immunogenic or noni-immunogenic) or recombinant nucleic acids encoding them may be included in a kit. The kit may also include one or more transfection reagents to facilitate delivery of circular RNAs (or recombinant nucleic acids encoding them) to cells. Such kits may also include components that preserve the polynucleotides or that protect against their degradation. Such components may be RNAse-free or protect against RNAses.

Such kits generally will comprise, in suitable means, distinct containers for each individual reagent or solution. The kit may comprise one or more containers holding the circular RNAs, or recombinant polynucleotides encoding them, and other agents. Suitable containers for the compositions include, for example, bottles, vials, syringes, and test tubes. Containers can be formed from a variety of materials, including glass or plastic. A container may have a sterile access port (for example, the container may be a vial having a stopper pierceable by a hypodermic injection needle).

The kit can further comprise a container comprising a pharmaceutically acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of treating immune diseases and conditions with circular RNAs, as described herein. The package insert can be an unapproved draft package insert or can be a package insert approved by the Food and Drug Administration (FDA) or other regulatory body.

In one embodiment, the kit comprises at least on immunogenic circular RNA (e.g., generated by splicing of an exogenous intron or splint ligation), or a recombinant nucleic acid encoding such a circular RNA, and optionally other reagents (e.g., transfection agents) for delivery of the circular RNA to a cell. In certain embodiments, the kit further comprises one or more immunogens or a vaccine. The kit may also comprise means for delivering the composition to a subject and instructions for treating immune diseases and conditions benefitting from an increased innate immunological response, such as cancer, an infection, or immunodeficiency.

In another embodiment, the kit comprises a non-immunogenic circular RNA (e.g., generated by splicing of an endogenous intron) comprising an IRES operably linked to an RNA sequence encoding a therapeutic polypeptide, or a recombinant nucleic acid encoding such a circular RNA, and optionally other reagents (e.g., transfection agents) for delivery of the circular RNA to a cell. The kit may also comprise means for delivering the composition to a subject and instructions for treating diseases and conditions benefitting from expression of the therapeutic polypeptide encoded by the circular RNA.

III. EXPERIMENTAL

Below are examples of specific embodiments for carrying out the present disclosure. The examples are offered for illustrative purposes only, and are not intended to limit the scope of the present disclosure in any way.

Efforts have been made to ensure accuracy with respect to numbers used (e.g., amounts, temperatures, etc.), but some experimental error and deviation should, of course, be allowed for.

Example 1

Sensing Self and Non-Self Circular RNAs

This Example describes results demonstrating that exogenous circular RNAs potently stimulate immune signaling, and mammalian cells sense self versus nonself circRNAs via circRNA biogenesis. Transfection of purified in vitro spliced circRNA into mammalian cells leads to potent induction of innate immunity genes. The nucleic acid sensor RIG-I is necessary and sufficient to sense foreign circRNA, and RIG-I and foreign circRNA co-aggregate in cytoplasmic foci. CircRNA activation of innate immunity is independent of 5' triphosphate, double-stranded RNA structure, or primary sequence of the foreign circRNA. Instead, self-nonself discrimination depends on the intron that programs the circRNA. Use of a human intron to express a foreign circRNA sequence abrogates immune activation, and human circRNA is associated with diverse RNA binding proteins reflecting its endogenous splicing and biogenesis. These results reveal innate immune sensing of circRNA, a prevalent class of host and pathogen RNAs, and highlight introns—the predominant output of mammalian transcription—as unexpected arbiters of self-nonself identity in the RNA world.

Methods

RNA Synthesis and Purification

Unmodified RNA was synthesized by in vitro transcription using an mMessage mMachine T7 transcription kit (Ambion, AM1344) following the manufacturer's instructions. Cy3-labeled RNA was synthesized by in vitro transcription using a MEGAscript T7 transcription kit (Ambion, AM1334) and adding Cy3-UTP (GE Healthcare, PA53026) in a 1:25 ratio with the transcription kit's CTP. Transcribed RNA was purified using a RNeasy Mini column (Qiagen), treated with FastAP (ThermoFisher Scientific, EF0652) following the manufacturer's instructions, and purified again using an RNeasy Mini column. Circular RNA was purified by treatment with RNase R (Epicenter, RNR07250) following the manufacturer's instructions. The quality of the RNA was assessed by agarose gel or Bioanalyzer (Agilent).

Cell Lines and Maintenance

Human HeLa (cervical adenocarcinoma) cells were grown in Dulbecco's modified Eagle's medium (DMEM, 11995-073) supplemented with 100 units/ml penicillin-streptomycin (Gibco, 15140-163) and 10% (v/v) fetal bovine serum (Invitrogen, 12676011). Cell growth was maintained at 37° C. in a 5% $CO_2$ atmosphere.

Plasmids

The plasmid containing the permuted intron-exon was a generous gift from Professor Manuel Ares, Jr. (University of California, Santa Cruz). Gibson assembly (NEB) was used to construct the self-splicing and ZKSCAN1 plasmids containing the GFP-IRES or mCherry exons. All plasmids were propagated in TOP10 E. coli competent cells (ThermoFisher Scientific) grown in LB medium and purified using the Maxi Plasmid DNA Purification Kit (Qiagen).

Transient Transfection

Cells were transfected at 70 to 80% confluence using Lipofectamine 2000 (Invitrogen, 11668-019). The nucleic acids and Lipofectamine 2000 were diluted and mixed in Opti-MEM (Invitrogen, 31985-088), incubated for 5 minutes at room temperature, the nucleic acids and Lipofectamine 2000 were mixed together, incubated for 15 minutes at room temperature and then the nucleic acids-Lipofectamine 2000 complexes were applied to the monolayer cultures. 500 ng of nucleic acids was transfected into one well of a 24-well plate.

RNA Extraction, Selection, Library Preparation, and Sequencing

Total RNA was isolated using TRIzol reagent (Life Technologies), according to manufacturer's instructions. RNA was re-suspended in ultrapure water and treated with DNAse I (Ambion, AM2222) for 30 minutes at 37° C. and subjected to RNA clean up with RNeasy Midi Kit (Qiagen), according to the manufacturer's instructions. RNA was eluted in ultrapure water. Total RNA was subjected to ribosomal RNA depletion with RiboMinus, and larger RNAs (>200nt) were enriched by selective binding to RNEasy Mini columns in the following ratio: 100 µl RNA in water to 350 µl RLT to 120 µl of 100% EtOH. The RNeasy manual was followed for washes and elution. Library preparation for high-throughput sequencing was performed following the library cloning method described in Flynn et al. (RNA (New York, N.Y.) 21, 135-143 (2015)). The following notes are minor deviations for RNAseq: Ribo-depleted RNA was fragmented to ~100 nucleotides by incubation for 45 seconds at 95° C. with Zinc chloride buffer (10 mM $ZnCl_2$, 10 mM Tris-HCl, pH 7.0). The reaction was stopped with 0.2M EDTA and immediately placed on ice. The fragmented RNA was recovered using the RNEasy Mini Kit (Qiagen). Fragmented RNA was treated with 10 Units of T4 PNK (New England Biolabs, Inc., M0201S), 1 Unit 30 of FastAP (ThermoFisher Scientific) in 1× PNK buffer with 40 Units of Ribolock RNase Inhibitor (Life Technologies, E00384) for 30 minutes at 37° C., to repair the 3' of the RNA. For the ligation of the 3' end adaptor, 0.8 µM of 3'-end biotin blocked preadenylated adaptor, 6.6 Units of T4 RNA ligase 1, high concentration (New England Biolabs, Inc., M0437M), in 1× RNA ligase buffer with 5 mM DTT and 50% PEG8000, were added, and the reaction was incubated at RT for 3 hours. To remove excess linker, 30 Units of RecJf (New England Biolabs, Inc., M0264L) and 20 Units of 5' Deadenylase (New England Biolabs, Inc., M0331S) in 1× RecJ buffer with Ribolock RNase Inhibitor were added to the reaction, and incubated for 1 hour at 37° C. The reaction was cleaned with RNA Clean & Concentrator columns (Zymo Research, R1016). Reverse transcription, biotin capture of ligated fragments, cDNA circularization, library amplification, and PAGE purification were carried out exactly as written in the previously published method. One microliter of each sample was used for quantification with Kapa Library quantification (Kapa Biosystems) and then sent for deep sequencing on the Illumina NextSeq for 1×75-bp cycle run.

RNA expression analysis: Libraries were separated by barcode, matching reads were collapsed and barcodes removed. For all libraries, single-end RNA-Seq reads were initially mapped against human ribosomal RNA. Reads aligning to the rRNA were discarded, and remaining reads were mapped to the human (hg19 assembly) genome using STAR (Dobin, A. et al. STAR: ultrafast universal RNA-seq aligner. *Bioinformatics* 29, 15-21, (2013)). Reads for each transcript were extracted using HTSeq (Anders, S., Pyl, P. T. & Huber, W. HTSeq—a Python framework to work with high-throughput sequencing data. *Bioinformatics* 31, 166-169, (2015)). Differential gene expression was calculated with DESeq2 (Love, M. I., Huber, W. & Anders, S. Moderated estimation of fold change and dispersion for RNA-seq data with DESeq2. Genome Biology 15, 550, (2014)). GO term enrichment was calculated with Metascape (Tripathi, S. et al. Meta- and Orthogonal Integration of Influenza; Data Defines a Role for UBR4 in Virus Budding. *Cell Host & Microbe* 18, 723-735).

Reverse Transcription and Real Time PCR Analysis

Total RNA was isolated from cells using TRIzol (Invitrogen) and an RNeasy Mini kit (Qiagen) following the manufacturers' instructions. Reverse transcription and quantitative real-time PCR analysis were performed in triplicate using Brilliant II SYBR Green qRT-PCR Master Mix (Agilent) and a LightCycler 480 (Roche). The mRNA levels were normalized to actin, GAPDH, or HPRT values.

TABLE 1 qPCR primers

| Species | Name | | Sequence |
|---|---|---|---|
| Human | Linear GFP | Forward | ACTACCTGAGCACCCAGTCC (SEQ ID NO: 1) |
| | | Reverse | CTTGTACAGCTCGTCCATGC (SEQ ID NO: 2) |
| | Circular GFP (self-splicing) | Forward | GATAAGCTTGCCACCTCAGTAGTG (SEQ ID NO: 3) |
| | | Reverse | ATCCATCACACTGGCATATGAC (SEQ ID NO: 4) |
| | Circular GFP (ZKSCAN) | Forward | GCTGACCCTGAAGTTCATCTG (SEQ ID NO: 5) |
| | | Reverse | CTTGTAGTTGCCGTCGTCCTT (SEQ ID NO: 6) |
| | RIG-1 | Forward | TGTGGGCAATGTCATCAAAA (SEQ ID NO: 7) |
| | | Reverse | GAAGCACTTGCTACCTCTTGC (SEQ ID NO: 8) |
| | MDA5 | Forward | GGCACCATGGGAAGTGATT (SEQ ID NO: 9) |
| | | Reverse | ATTTGGTAAGGCCTGAGCTG (SEQ ID NO: 10) |
| | OAS | Forward | GCTCCTACCCTGTGTGTGT (SEQ ID NO: 11) |
| | | Reverse | TGGTGAGAGTACTGAGGAAGA (SEQ ID NO: 12) |
| | OASL | Forward | AGGGTACAGATGGGACATCG (SEQ ID NO: 13) |
| | | Reverse | AAGGGTTCACGATGAGGTTG (SEQ ID NO: 14) |
| | PKR | Forward | TCGCTGGTATCACTCGTCTG (SEQ ID NO: 15) |
| | | Reverse | GATTCTGAAGACCGCCAGAG (SEQ ID NO: 16) |

TABLE 1-continued qPCR primers

| Species | Name | | Sequence |
|---|---|---|---|
| | INFb | Forward | CTCTCCTGTTGTGCTTCTCC (SEQ ID NO: 17) |
| | | Reverse | GTCAAAGTTCATCCTGTCCTTG (SEQ ID NO: 18) |

Flow Cytometry

Cells were stained with Annexin V-FITC (BD Pharmingen, 556420) following the manufacturer's instructions. Cells were processed and analyzed on a special order FACS Aria II (BD Biosciences).

Western Blot Analysis

HeLa cells were collected and lysed 24 hours after transfection to extract total proteins. RIPA buffer (150 mM sodium chloride, 1% Triton X-100, 0.5% sodium deoxycholate, 0.1% sodium dodecyl sulfate, 50 mM Tris, pH 8.0) was used to lyse the cells. Proteins were fractionated by sodium dodecyl sulfate polyacrylamide gel electrophoresis (SDS-PAGE), transferred to nitrocellulose membranes, blocked in phosphate-buffer saline containing 3% (wt/vol) nonfat milk for 1 hour at room temperature, and then incubated overnight at 4° C. with the indicated primary antibody. Rabbit polyclonal antibody was used to detect RIG-I (Cell Signaling Technology, 3743S) and goat polyclonal IgG antibody was used to detect actin (Santa Cruz Biotechnology, SC-1616). IRDye 800CW Goat anti-rabbit IgG (Li-Cor, 926-32211) or IRDye 680CW Donkey anti-goat IgG (Li-Cor, 926-68074) secondary antibodies were used according to the manufacturer's instructions. Western blot detection and quantification was done using an Odyssey infrared imaging system (Li-Cor).

Immunofluorescence

HeLa cells were grown on 8-well Nunc Lab-Tek Chamber Slide system (Sigma-Aldrich, C7182-1CS) and transient transfection of Cy3-RNA was performed as described above. Cells 80-90% confluent were fixed with 1% formaldehyde (Sigma-Aldrich) for 10 minutes at room temperature. The formaldehyde fixed slide was rinsed in PBS and permeabilized in PBS 0.5% Triton-X 100 for 10 minutes at room temperature. Then, the slide was blocked with antibody dilution reagent (ThermoFisher Scientific, 00-3218) for 1 hour at room temperature. Rabbit polyclonal primary antibody (Cell Signaling Technology, 3743S) was diluted in antibody dilution reagent 1:500, and incubated overnight at 4° C. After washing with PBS containing 0.05% Tween-20 for 3 times, 10 minutes each, slides were incubated with secondary antibodies goat anti-rabbit-Atto647N (Sigma-Aldrich, 50185-1ML-F), for 45 minutes at room temperature. The slides were washed with PBS containing 0.05% Tween-20 for 3 times 10 minutes each, mounted using Vectashield with DAPI (Vector Labs, H-1200) and imaged with Leica SP8.

Image Analysis

Images were taken under Leica SP8, and the colocalization analysis was performed with Volocity software (PerkinElmer). In brief, the signal intensity and area from both Cy3 and RIG-I were measured in the Measurement function, and the intersection of the two channels was used to defined overlapping area. The Overlapping fraction was calculated with following equation: Overlapping fraction=interest area/total area from two channels. ~45 cells with independent replicates were measured and p value was calculated using Student's t-test.

Construction and Validation of RIG-I−/− in HeLa Cells

CRISPR target sequence of RIG-I was chosen using casoffinder (rgenome.net/casoffinder/) to have less than 4 mismatches for NGG PAM sequence. The self-complementary oligonucleotides (acaccgGATTTCTGCTGTTCATA-CACg (SEQ ID NO:19) and aaaacGTGTAT-GAACAGCAGAAATCcg (SEQ ID NO:20), ordered from Elim Biopharm) targeting a portion of DDX58 (GATTTCTGCTGTTCATACAC, SEQ ID NO:21) were annealed, and ligated into BsmbI-digested MLM3636 (Addgene #43860) to create a plasmid that transcribes the guide RNA. 650 ng of MLM3636 containing the DDX58 target sequence and 650 ng of p3s-Cas9HC (Plasmid #43945) were transiently transfected into 24-well plates of HeLa as described above. After 48 hours, colonies were plated in 96-well with a density of 0.3 cells/well for single colony isolation. To validate RIG-I knockout clones, genomic DNA was isolated during subculture using DNeasy Blood & Tissue Kit (Qiagen). DDX58 locus containing the target sequence was amplified by PCR (Forward: GGCTGTTGG-CATGCTACTTA (SEQ ID NO:22), Reverse: CCT-TAGCACAGAGCCTGACA (SEQ ID NO:23), and nested Forward: TCAGCTCAGTGGTATTAGAAGAGC (SEQ ID NO:24), nested Reverse: TGTGCCACGTAAACATCAAA (SEQ ID NO:25)) followed by T7 Endonuclease I (New England Biolabs Inc., M0302L) digestion. For the T7 Endonuclease I assay, add 9 μL of PCR reaction (from 20 μL total) to 2 μL NEB buffer 2, 0.5 μL T7 Endonuclease I, and water to 20 μL. Incubate at 37° C. for 30 minutes. The entire sample was loaded immediately for gel electrophoresis analysis. Clones with appropriate T7 Endonuclease I activity were sequenced by MiSeq, after amplifying by PCR (Forward: GGGGAAAGTTGTCTTTTTTGC (SEQ ID NO:26), Reverse: TACCTACCCATGTCTTTCAAAGTATT (SEQ ID NO:27)) followed by True-seq adaptor ligation. Clones that did not contain an in-frame deletion or wild-type sequence, according to MiSeq sequencing, were probed by Western to assess for the presence of the RIG-I protein.

ChIRP-Mass Spectrometry

ChIRP-mass spectrometry was conducted as previously described in Chu et al. (Systematic Discovery of Xist RNA Binding Proteins. *Cell* 161, 404-416, (2015). Mass spectrometry was conducted at Stanford Mass Spectrometry Facility.

TABLE 2

Probes

| Probe # | Probe (5'→3') |
|---|---|
| 1 | GGGAGGTTTTATGATGTGTT (SEQ ID NO: 28) |
| 2 | CAGGAACTGACTTGATCCAA (SEQ ID NO: 29) |

TABLE 2-continued

Probes

| Probe # | Probe (5'→3') |
|---|---|
| 3 | CTATTACGATACCATCCTTC (SEQ ID NO: 30) |
| 4 | GAATATCTCTGGGTCTGGAG (SEQ ID NO: 31) |
| 5 | CCACTGATGACAAAGTTCCT (SEQ ID NO: 32) |
| 6 | CAGAAGCTCCAGGATCTGTT (SEQ ID NO: 33) |
| 7 | ATCAAGCTCCAAGTCTTCTA (SEQ ID NO: 34) |
| 8 | GAAGGTCAAAGCTCGAGGAC (SEQ ID NO: 35) |

Results

Figure 1B:
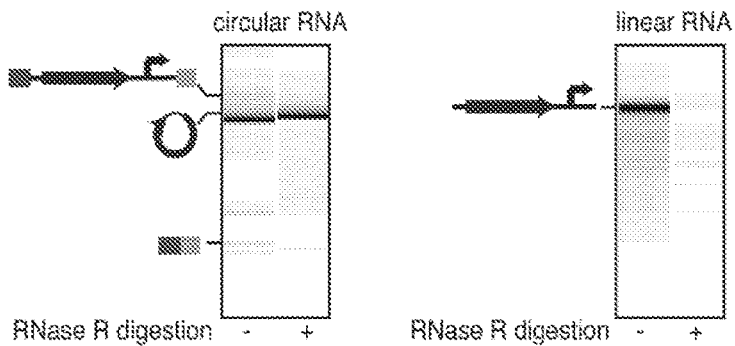
Figure 1C:
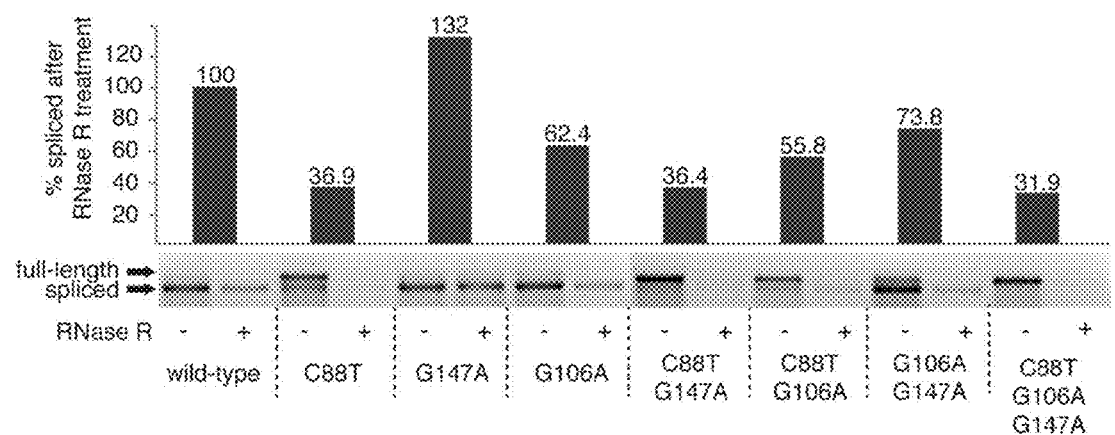
Figure 1D:
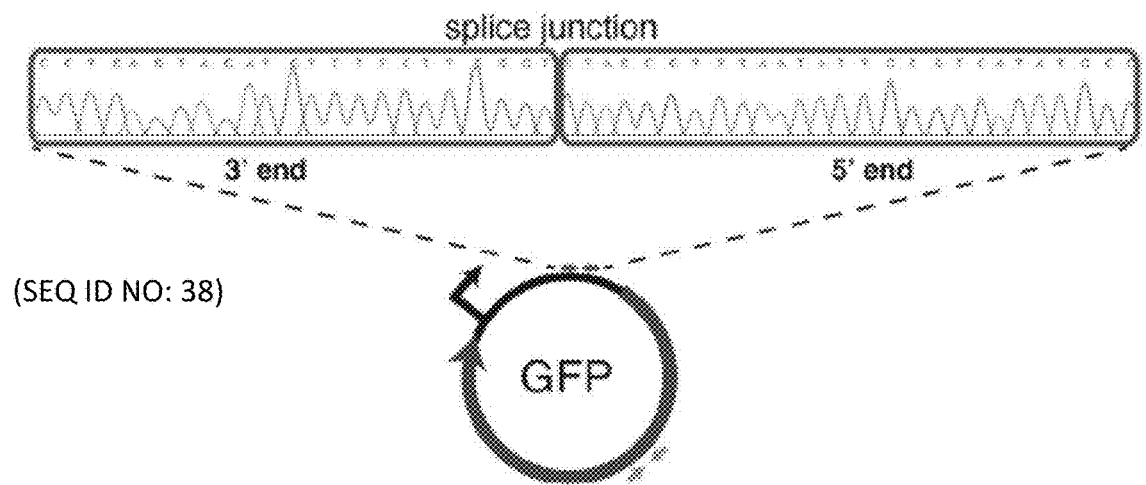

In vitro production of circRNAs was programmed with self-splicing introns (FIG. 1A). Group I intron of phage T4 thymidylate synthase (td) gene is well characterized to circularize while the exons splice together 8-10. When the td intron order is permuted (5' half placed at the 3' position and vice versa) flanking any exon sequence, the exon is circularized via two autocatalytic transesterification reactions (Ford, E. & Ares, M. Synthesis of circular RNA in bacteria and yeast using RNA cyclase ribozymes derived from a group I intron of phage T4. *Proceedings of the National Academy of Sciences* 91, 3117-3121, (1994); Puttaraju, M. & Been, M. D. Generation of nuclease resistant circular RNA decoys for HIV-Tat and HIV-Rev by autocatalytic splicing. *Nucleic acids symposium series*, 49-51 (1995). Destabilized GFP followed by the Encephalomyocarditis Virus (EMCV) internal ribosome entry site (IRES) as the exon was used. Successful circRNA production is monitored by quantitative polymerase chain reaction (qPCR) analysis with divergent primers (FIG. 1A, dark gray) that span the splice junction and only amplifies product when circRNA is present. Convergent primers (FIG. 1A, light gray) detect both the linear and circRNA. Circularization also brings the IRES upstream of GFP sequence, allowing protein translation. Following in vitro transcription, the permuted self-splicing introns produce a 1.5 kilobase circRNA (SEQ ID NO:36). A control linear RNA has the same sequence as the circRNA; both linear and circRNAs were treated with phosphatase so there are no 5' phosphates present in either sample. The circRNA product is resistant to digestion with the exonuclease RNase R while linear RNA template and side products were depleted (FIG. 1B). RNase R treatment was used to purify circRNA in all subsequent experiments. CircRNA production proceeds via group I self-splicing, because known point mutations that reduce td intron splicing efficiency correspondingly reduced circRNA yield (FIG. 1C). Direct sequencing of the circRNA splicing junction confirmed a uniform splice junction, precisely at the expected autocatalytic splice site (FIG. 1D). Thus, phage self-splicing intron enables in vitro production of circRNAs that are suitable for mammalian expression.

In the course of investigating circRNA as a vehicle for ectopic gene expression, it was unexpectedly discovered that it has potent immune stimulatory property. When purified unmodified or Cy3-labeled circRNA was transiently transfected into HeLa cells, very little GFP expression and, surprisingly, significantly more cell death in the cells containing circRNA than linear RNA encoding the same sequence was observed. This effect required intracellular introduction of circRNA via transfection; adding circRNA to the media had no effect. Transfection of in vitro transcribed linear RNA is known to induce innate immune signaling (Warren et al., Cell Stem Cell 7, 618-630 2010), but such an effect was not known for circRNAs. RNA-seq of HeLa cells transiently transfected with linear or circRNA showed that circRNA more potently stimulated the expression of genes involved in innate immunity; the top enriched Gene Ontology terms include response to cytokine, regulation of cytokine production, cellular response to virus, and NF-kB signaling (FIG. 2A). 127 genes were significantly induced by either linear or circRNA transfection (induced 4-fold, $p<0.05$, FDR<0.1), and the majority of these genes were significantly more induced by circRNA than linear RNA transfection (84 observed versus 64 expected by chance alone, $p=0.00016$, hypergeometric distribution; FIG. 2A).

CircRNA-induced genes include well known innate immunity regulators such as retinoic-acid-inducible gene-I (RIG-I, also known as DDX58), melanoma-differentiation-associated gene 5 (MDA5, also known as IFIH1), 20-50 oligoadenylate synthase 1 (OAS1), OAS-like protein (OASL), and, to a lesser extent, protein kinase R (PKR). To confirm the RNA-seq results, linear or circRNA was transfected into HeLa cells, washed extensively after 24 hr to remove unincorporated RNA, and isolated total RNA for qRT-PCR. The expression of a panel of innate immune genes relative to actin and the levels of transfected circular and linear RNAs inside cells were measured for normalization to account for the differences between linear and circRNA transfection efficiency and stability for all subsequent assays (STAR Methods). CircRNA potently stimulates the expression of several innate immunity genes (e.g., ~500-fold for RIG-I and 200-fold for OASL mRNA) and more potently than linear RNA of the same sequence or mock transfection control (FIG. 2B). RIG-I induction by circRNA was also confirmed on the protein level. Transfection of circRNA also induced innate immunity genes in a keratinocyte cell line (HaCaT) and a mouse macrophage cell line (RAW 264.7). These results indicate circRNA is an inducer of innate immunity signaling.

To test if the immunogenic response stimulated by circRNA transfection affects the ability of a virus to infect HeLa cells, cells were transfected with linear or circRNA labeled with Cy3, and after 24 hours, cells were exposed to Venezuelan equine encephalitis virus harboring a green fluorescent protein reporter gene (VEEV-GFP, a +ssRNA virus). Cy3-labelled circular or linear RNA induced immune genes similarly to their unlabeled counterparts. FACS analysis showed mock treated cells and cells with linear RNA were infected to similar levels, while cells transfected with circRNA had a 10-fold lower VEEV-GFP infection rate (FIGS. 2C and 2D). Additionally in cultures transfected with circRNA, neighbor cells that did not contain transfected circRNA also had decreased infection levels, similar to cells that had circRNA (FIG. 2E). This collective, cell non-autonomous protection from virus infection is consistent with the ability of foreign circRNA to induce antiviral cytokines such as interferon-beta. Collectively, these results show that sensing of exogenous circRNA can confer functional immune protection against a viral pathogen.

Figures 3A, 3B, 3C:
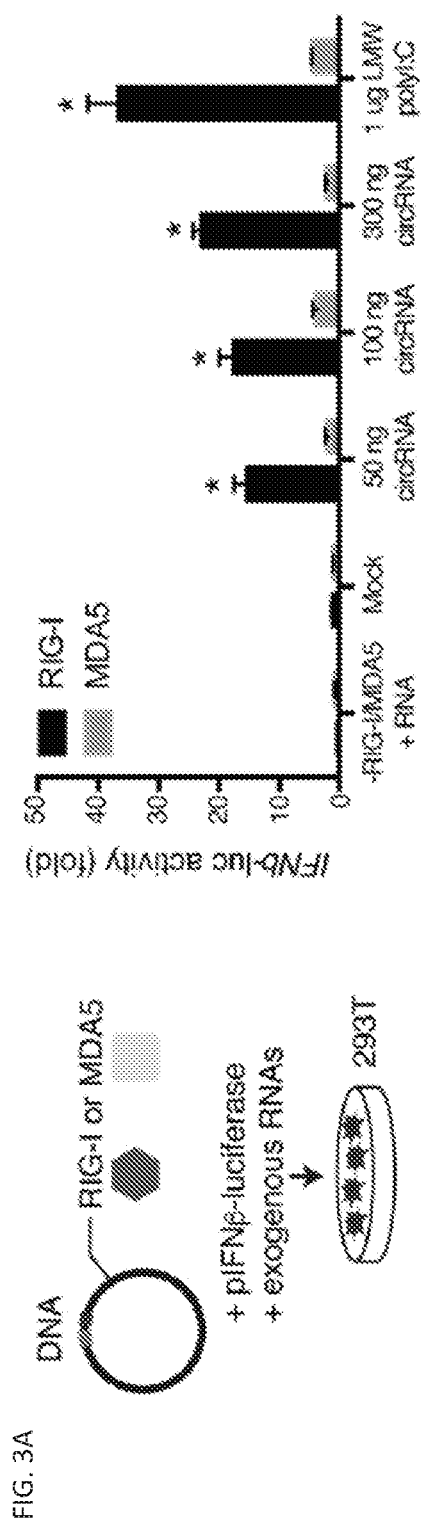

RIG-I and MDA5 are two well-known intracellular sensors of foreign RNAs in mammalian cells. RIG-I is activated by short "panhandle" RNA structure with 5'triphosphate while MDA5 is activated by long double-stranded RNAs (Hornung, V. et al. 5'-Triphosphate RNA Is the Ligand for RIG-I. *Science* (New York, N.Y.) 314, 994-997, (2006); Kato, H. et al. Length-dependent recognition of double-stranded ribonucleic acids by retinoic acid-inducible gene-I and melanoma differentiation associated gene. *The Journal of Experimental Medicine* 205, 1601-1610, (2008)). Neither of these features is known to exist in circRNA. To investigate which cytosolic foreign nucleic acid sensor may detect exogenous circRNA, HEK293T cells that require exogenous RIG-I or MDA5 to be added for sensing exogenous RNAs were used. It was found that expression of RIG-I, but not MDA5, conferred responsiveness to circRNA in 293T cells, as evidenced by a ~20-fold induction of IFNB-reporter gene (FIG. 3A). Quantitative comparison with low molecular weight polyI:C (range 0.2-1 kb length), which activates RIG-I strongly and MDA5 weakly, showed that accounting for molarity, circRNA is approximately 10-fold more potent than polyI:C in immune gene stimulation. In contrast, MDA5 expression conferred strong responsiveness to long dsRNA but not circRNA, indicating distinct signaling requirements.

Next, the requirement of RIG-I in sensing circRNA was investigated. Transfection of wild-type or RIG-I knockout (KO) MEFs (Kato et al., Immunity 23, 19-28 2005) showed that RIG-I KO completely abrogated circRNA-induced innate immune genes (FIG. 3B). RIG-I KO MEFs are still inducible by interferon stimulatory DNA, showing that RIG-I is needed in a proximal step of circRNA sensing. HeLa cells knocked out for human RIG-I by CRISPR-Cas9 technology were generated and it was found that human RIG-I KO also substantially reduced the response of innate immunity genes to circRNAs (FIG. 3C). These results show that RIG-I is necessary and sufficient to sense foreign circRNA in the cell types examined.

To probe whether RIG-I may directly sense circRNAs, immunofluorescence microscopy of Cy3-labeled transfected RNA and endogenous RIG-I was performed (FIG. 3D). It was found that RIG-I in cells with transfected circRNA formed more and larger intracellular foci compared to with linear RNA (p<0.05 for each; FIG. 3E). Notably, circRNA was significantly more likely to colocalize in RIG-I foci than linear RNA (FIG. 3F). The colocalized foci typically have RIG-I signal in the center surrounded by circRNA and are distributed throughout the cytoplasm. These results implicate RIG-I in the proximal sensing of circRNA. Because RIG-I is itself induced by circRNA and needed to sense circRNA, circRNA induction of RIG-I may constitute a positive feedback loop. RIG-I may directly sense circRNA, or it may be required for a proximal signal amplification step for immune gene induction.

Figure 4A:
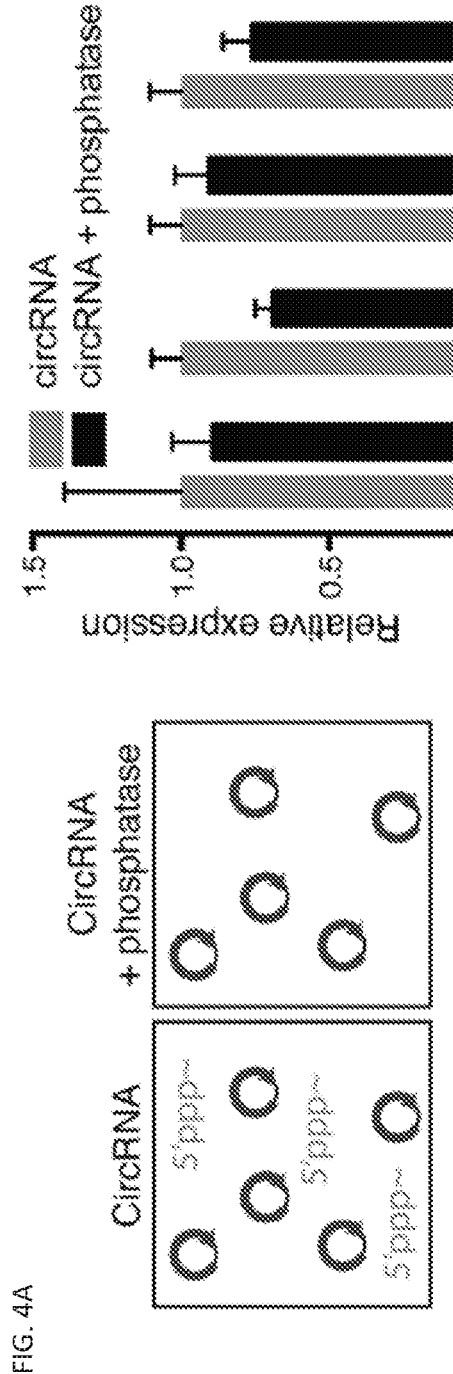
FIGS. 4A-4D shows that circRNA stimulation of innate immune genes is not explained by known RIG-I ligands.
Figure 4B:
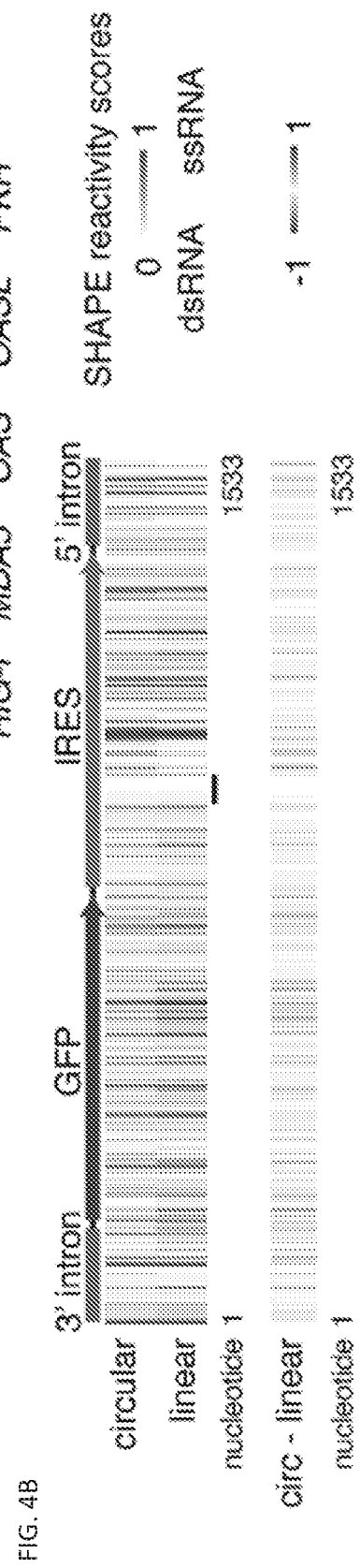

How may circRNA activate RIG-I was investigated. The known pathogen-associated molecular pattern (PAMP) for RIG-I includes a 5' triphosphate on RNA (Hornung et al., supra). By definition, circRNA does not have a 5' end, and treatment of the circRNA preparation with phosphatases that selectively cleaves 5' phosphates did not diminish its ability to stimulate innate immune genes (FIG. 4A). As positive control, phosphatase treatment of 50 triphosphate-containing linear RNA greatly reduced its immune signaling activity. These results indicate that circRNA activation of RIG-I is not due to contaminating triphosphates that are present in the circRNA preparation. In addition, long double-stranded RNA (dsRNA) can activate immune signaling (typically via MDA5 rather than RIG-I). The possibility that circularization may cause significant differences in secondary structure that lead to innate immune gene activation was investigated with in vitro selective 20-hydroxyl acylation and profiling (SHAPE) experiments, whereby single-stranded bases are mapped by high SHAPE reactivity (Spitale et al., Nature 519, 486-490 2015). Sequencing of the SHAPE libraries showed that in vitro-folded linear and circRNA, arising from the same primary sequence, have nearly identical SHAPE reactivity scores, showing that they may have comparable secondary structures (FIG. 4B). There was also no difference in the longest consecutive stretch of dsRNA in circular or linear RNA (38 versus 39 bases; FIG. 4B). Thus, sensing of circRNA is independent of known PAMPs of foreign RNAs.

Figures 4C, 4D:
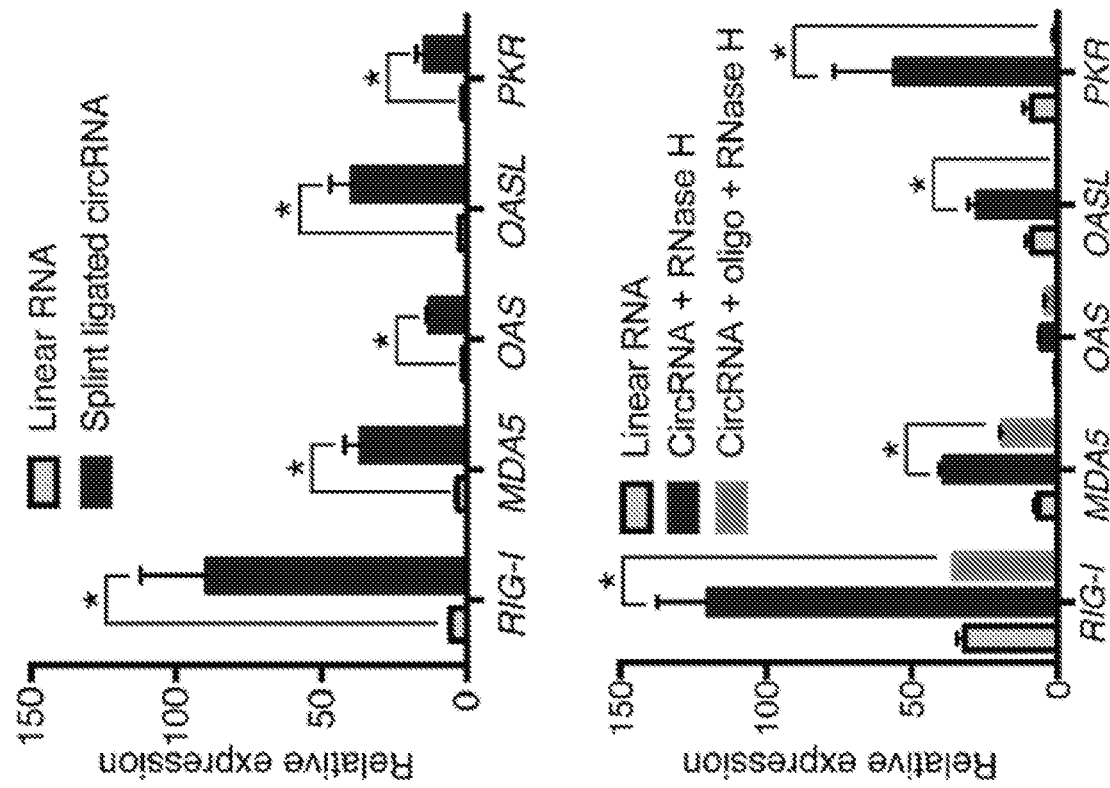

Two additional experiments were performed to rule out the possibility that aberrant, unknown products in the preparation of circRNA may cause immune stimulation. First, circRNA generated by in vitro splint ligation (without using the autocatalytic splicing td intron) also induced innate immune genes (FIG. 4C), indicating that any circRNA not generated by mammalian splicing is perceived as foreign. Second, after circRNA production by in vitro transcription and purification, a complementary DNA oligonucleotide and RNase H was used to specifically cleave the circRNA. Linearization of circRNA abrogated its immune stimulatory property (FIG. 4D), indicating that it is indeed the circRNA and not any other product that is responsible for the immune activation. Taken together, these experiments demonstrate that the circular properties of the RNA cause immune gene stimulation.

Next, the feature of circRNA required to activate innate immune gene expression was mapped using a phage td intron to produce circular and linear RNA in vitro containing only the mCherry coding sequence—replacing the entire exonic sequence of IRES-GFP circRNA. The mCherry circRNA potently simulated innate immune genes over linear RNA and control, similar to IRES-GFP circRNA (FIG. 4A). These results show that immune activation is based on the circularity of the RNA rather than the primary sequence or ribosome binding by the IRES. If the circRNA exon does not define "self" versus "nonself", the only remaining feature is the intron that programs the circularization. A DNA construct that expresses the phage self-splicing IRES-GFP circRNA, and a version without the second intron half, making it only form linear RNA was constructed. It was found that DNA-programmed expression still induced robust immune gene activation, highlighting a potent mode of circRNA induction of immune genes (~600-fold over linear RNA; FIG. 5A). The GFP-IRES circRNA exon and endogenous human ZKSCAN1 introns (Liang and Wilusz, Genes Dev. 28, 2233-2247 2014), which do not have autocatalytic-splicing properties (FIG. 5A) were next used. Complementary Alu repeats are present in these flanking introns, which enable human ZKSCAN1 to splice GFP-IRES into a circRNA. The linear control is the vector missing a portion of the upstream ZKSCAN1 intron so that base pairing of the 50 and 30 introns and circularization wouldnot occur. The full-length KSCAN1 introns led to copious production of GFP-IRES circRNA (confirmed by qRT-PCR and used for normalization), but completely abrogated innate immune gene induction (FIG. 5A). These results show that splicing by a "self intron" in human cellsconfers self-identity to circRNAs irrespective of their exonic sequence, and distinguishes endogenous circRNAs from foreign nucleic acids.

The properties of the foreign circRNA sensing mechanism were further investigated. First, transfection of a DNA construct encoding the *Drosophila* laccase2 introns (Kramer et al., *Genes Dev.* 29, 2168-2182 2015) flanking GFP-IRES exon into HeLa cells programmed circRNA production, as confirmed by qRT-PCR, but did not stimulate innate immune genes (FIG. 5B). Thus, because circRNA programmed by *Drosophila* introns but processed by the human spliceosome is sensed as "self" it is likely that the human splicing machinery or an associated process—rather than the sequence of human intron itself—confers self-identity to endogenously produced circRNAs. Second, encoding both td and ZKSCAN1 introns on the same RNA molecule yielded circRNA products that did not activate innate immune genes (FIG. 5C).

The same result is obtained with human introns either flanking phage intron or nested within phage intron. This result indicates that the "self circRNA" identity conferred by human introns is dominant over the foreign identity. Third, co-expression of ZKSCAN1 intron-programmed circRNAs and td circRNAs in the same cells still led to immune gene activation, indicating that human intron-mediated protection of immune activation operates solely in cis and lacks transitive property.

Figure 6A:
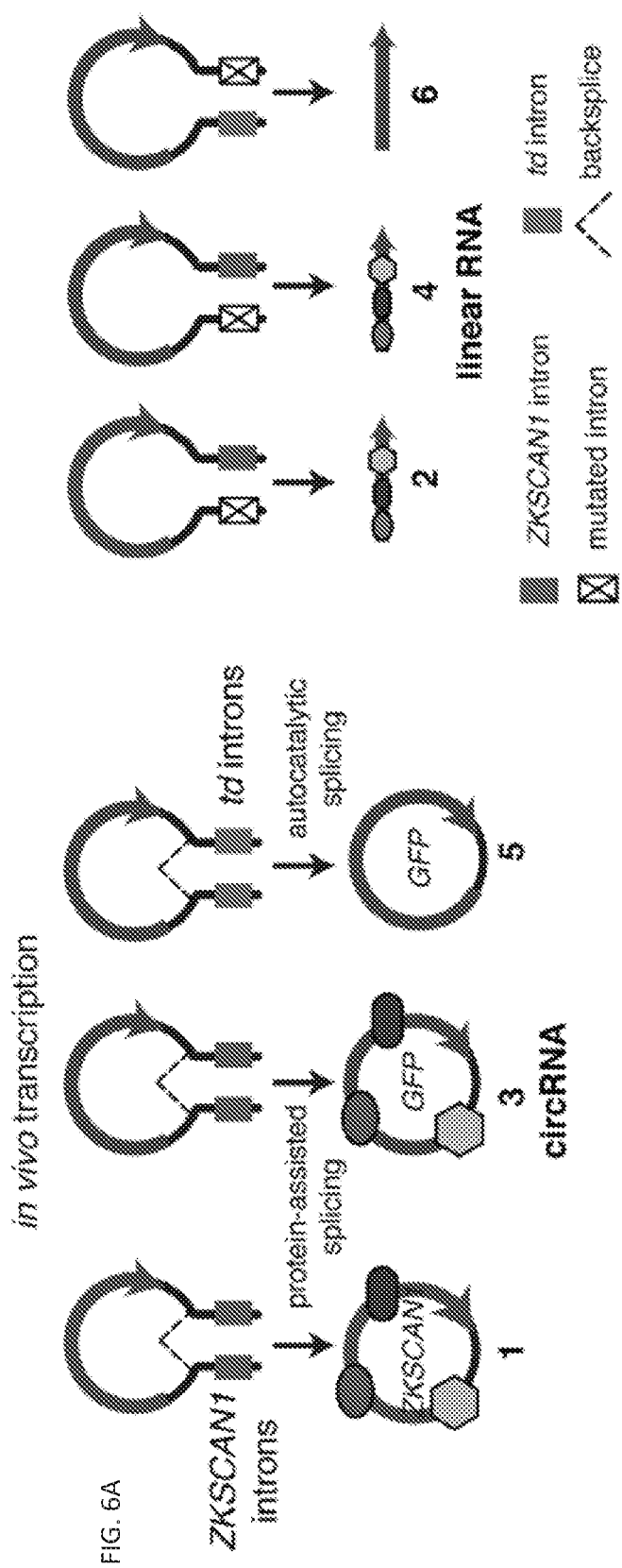
FIGS. 6A-6D shows that splicing mechanism determines self versus non-self circRNA.

To understand how endogenous human circRNA may be marked, Comprehensive Identification of RNA binding Proteins by Mass Spectrometry (ChIRP-MS) (Chu, C. et al. Systematic Discovery of Xist RNA Binding Proteins. *Cell* 161, 404-416, (2015)) was performed to compare proteins that are associated with a model circular or linear RNA. HeLa cells were transfected with DNA plasmids encoding RNAs with combinations of (i) ZKSCAN1 or phage td introns, which direct protein-assisted splicing or autocatalytic splicing, respectively; (ii) ZKSCAN1 endogenous exons or the GFP-IRES exon; (iii) control linear RNAs that lack one of the flanking introns required for back splicing or circRNAs with full introns (FIG. 6A). The endogenous ZKSCAN1 circRNA arises from a canonical "forward splice" between exons 2 and 3 and a "back splice" from the of exon 3 back to the 50 of exon 2 (Liang and Wilusz, 2014; supra); the mix of forward and back splice typifies most circRNAs (Jeck and Sharpless, Nat. Biotechnol. 32, 453-461 2014; Jeck et al., RNA 19, 141-157 2013; Salzman et al., PLoS ONE 7, e30733 2012). After DNA transfection, FISH against td-intron programmed circGFP-IRES was performed and the circRNA were found to be predominantly localized to the cytoplasm. Cells were crosslinked with formaldehyde to trap endogenous complexes; oligonucleotide probes were used to isolate ZKSCAN1 or GFP-IRES RNA products, along with their associated proteins. The oligonucleotide probes are directed against the exonic sequences only; hence, this experiment tests the consequence of introns on the subsequent fate of RNA binding proteins that associate with circRNA.

Figure 6B:
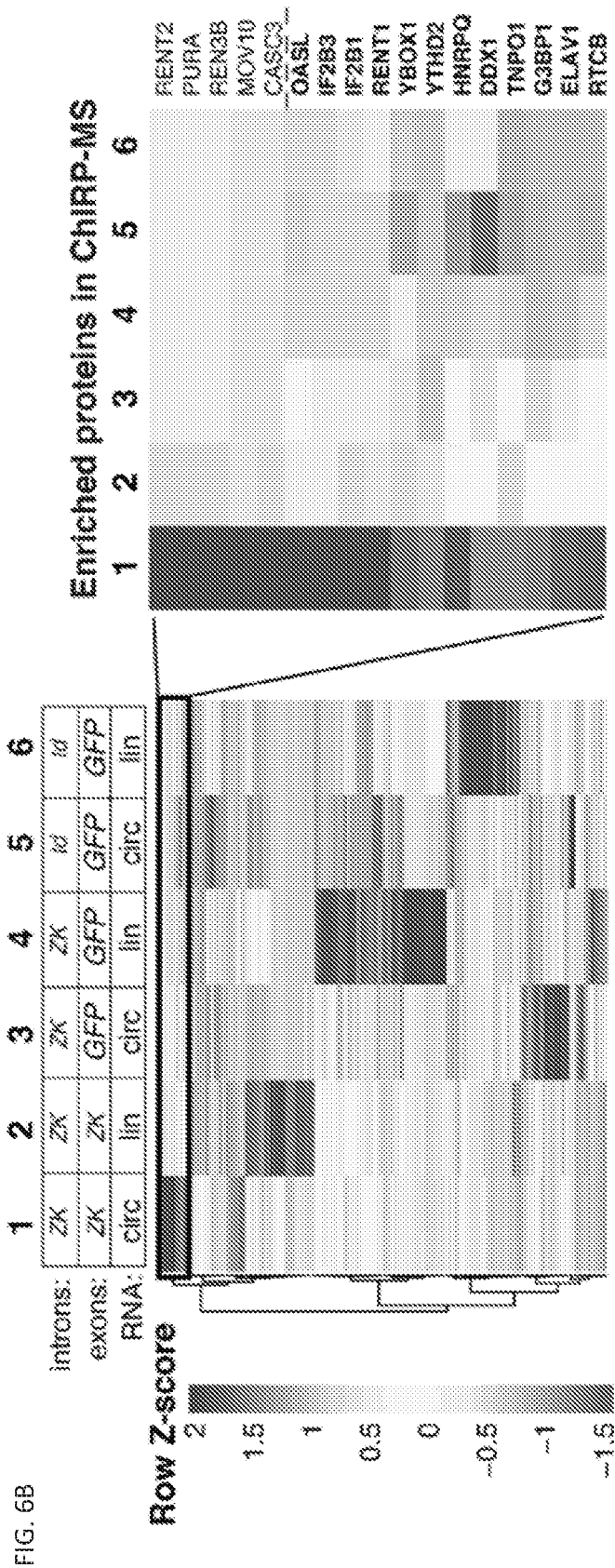
Figure 6D:
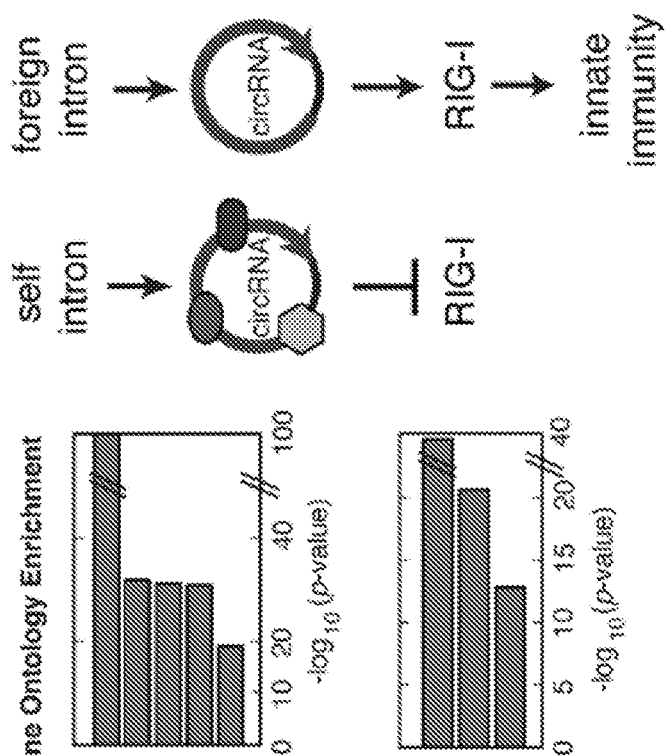
Figure 6C:
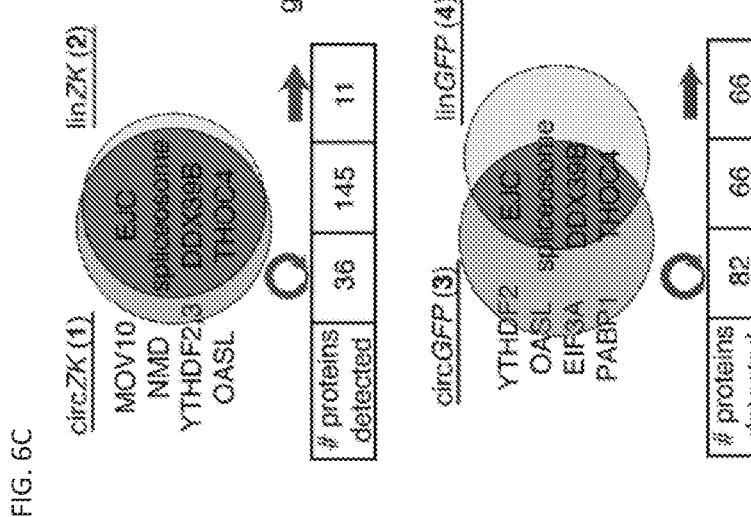

Following mass spectrometry to identify the proteins, enrichment was defined as containing ten or more spectral counts with 4-fold or greater than the RNase-treated negative control. Both circular and linear ZKSCAN1 RNAs were associated with a large and common set of RNA binding proteins (145 of 192 RBPs (75%) involved in RNA splicing, ribonucleocomplex assembly, and nucleic acid transport (lane 1 versus lane 2 in FIG. 6B). The shared RBPs include multiple components of the spliceosome (e.g., U1, U2, and U4/U6/U5 tri-snRNP subunits), the exon junction complex that is deposited as splice junctions (EIF4A3, MGN2, RNPS1), and factors that mediate nuclear export of RNAs (DDX39B, THOC4, XPOS). In addition, a set of 36 proteins that are at least 3-fold more enriched on circZKSCAN1 than linear ZKSCAN1 RNA (FIG. 6C) was found. These include MOV10, a RNA helicase required for replication of HDV circRNA genome (Haussecker et al., Nat. Struct. Mol. Biol. 15, 714-721 2008) and RNA interference (Tomari et al., Cell 116, 831-841 2004), components of the nonsense-mediated decay pathway (UPF1, UPF2), RNA N6-methyladenosine reader proteins (YTHDF2, YTHDF3) (Dominissini et al., Nature 485, 201-206 2012), and the antiviral protein OASL.

To identify proteins associated with RNAs recognized as "self," ZKSCAN1 intron-directed linear and circRNAs were compared. Many of the proteins common to the ZKSCAN1 introns expressing endogenous ZKSCAN1 exons were also detected in the ChIRP-MS results from ZKSCAN1 introns expressing a foreign GFP-IRES exon (lane 1 versus lane 3 in FIGS. 6B and 6C). This demonstrates that the introns direct the placement of RBPs onto the circular and linear RNAs. The proteins unique to circGFP-IRES generated by ZKSCAN1-directed circularization also overlap with the circZKSCAN1, whereas the circGFP-IRES generated by td directed circularization have very few proteins associated (lane 3 versus lane 5 in FIG. 6C). No RIG-I associated with the autocatalytically spliced circRNA, was detected, indicating that the interaction is transient and was not captured by the ChIRP-MS.

Thus, a diverse and distinctive set of RBPs associate with endogenously produced human circRNA. Recent identification of m6A-marked endogenous human circular RNAs is fully consistent with this observation (Molinie et al., Nat. Methods 13, 692-698 2016; Yang et al., Cell Res. 27, 626-641 2017). These results demonstrate that introns program the protein cargos of circular RNAs, and also refine the set of RNA binding proteins that can mark the circRNA as "self."

Example 2

This Example demonstrates that circular RNA induces immunity in living animals. CircRNA can induce both cytotoxic T cells and antibody response. The circular RNA is active either delivered as naked RNA or encapsulated in liposomes.

Figure 7:
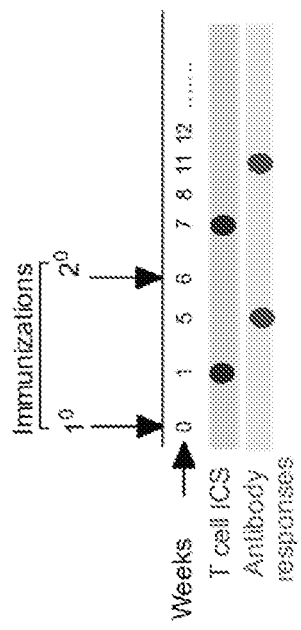
FIG. 7 shows a schedule of vaccination experiments in mice.

Vaccination experiments were performed as shown in Tables 3 and 4 below. To test efficacy of adjuvant for vaccination against ovalbumin (OVA) protein, animals (mice) were injected subcutaneously with OVA and one or more adjuvants. Positive controls for vaccination were injections of OVA with alum or poly (I:C). Different amounts of adjuvants were tested to investigate dose responsiveness. FIG. 7 shows the schedule of vaccinations.

TABLE 3

| Experimental groups | # of animals | Immunogen @ 100 micrograms dose | Adjuvant | Dose of adjuvant | Route of vaccination |
| --- | --- | --- | --- | --- | --- |
| 1 | 5 | Untreated control | | | |
| 2 | 5 | Ovalbumin | Alum | 150 µg | Sub cutaneous |
| 3 | 5 | Ovalbumin | poly (I:C) | 25 µg | Sub cutaneous |
| 4 | 5 | Ovalbumin | circRNA alone | 25 µg | Sub cutaneous |
| 5 | 5 | Ovalbumin | circRNA + Jet PEI (PolyplusTransfection) | 25 µg | Sub cutaneous |
| 6 | 5 | Ovalbumin | circRNA + Jet PEI (PolyplusTransfection) | 2.5 µg | Sub cutaneous |

TABLE 3-continued

| Experimental groups | # of animals | Immunogen @ 100 micrograms dose | Adjuvant | Dose of adjuvant | Route of vaccination |
|---|---|---|---|---|---|
| 7 | 5 | Ovalbumin | circRNA + Jet PEI (PolyplusTransfection) | 0.25 µg | Sub cutaneous |
| 8 | 5 | Ovalbumin | circRNA + GenJet Reagent | 25 µg | Sub cutaneous |
| 9 | 5 | Ovalbumin | RNA + GenJet Reagent | 2.5 µg | Sub cutaneous |

TABLE 4

| Experimental groups | # of animals | Immunogen @ 100 micrograms dose | Adjuvant | Dose of adjuvant | Route of vaccination |
|---|---|---|---|---|---|
| 1 | 5 | Untreated control | | | |
| 2 | 5 | Ovalbumin | Alum | 150 µg | Sub cutaneous |
| 3 | 5 | Ovalbumin | poly (I:C) | 25 µg | Sub cutaneous |
| 4 | 5 | Ovalbumin | circRNA alone | 25 µg | Sub cutaneous |
| 5 | 5 | Ovalbumin | circRNA + Jet PEI (PolyplusTransfection) | 25 µg | Sub cutaneous |
| 6 | 5 | Ovalbumin | circRNA + GenJet Reagent | 25 µg | Sub cutaneous |
| 7 | 5 | Ovalbumin | m6A-modified circRNA) | 25 µg | Sub cutaneous |
| 8 | 5 | Ovalbumin | m6A-modified circRNA + PEI or Genjet | 25 µg | Sub cutaneous |
| 9 | 5 | Ovalbumin | Linear RNA alone | 25 µg | Sub cutaneous |
| 10 | 4, MAVS KO | Ovalbumin | circRNA alone | 25 µg | Sub cutaneous |

Figure 8:
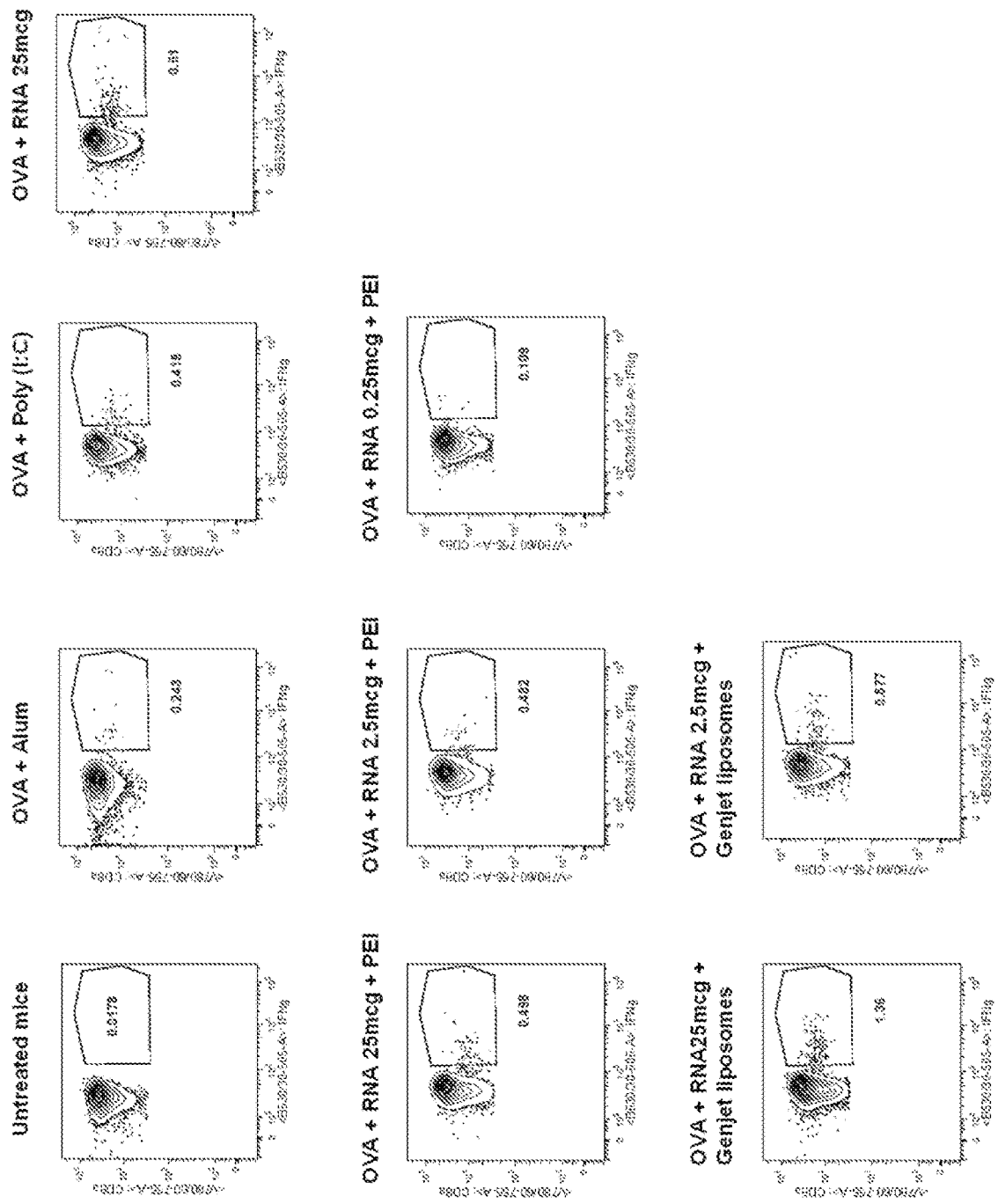
FIG. 8 shows representative flow plots of IFN-γ secreting OVA-specific CD8+ T cells in blood after primary vaccination.

Results are shown in FIGS. 8-11. FIG. 8 shows representative flow plots of IFN-γ secreting OVA-specific CD8+ T cells in blood after primary vaccination for Study #1 (Table 3). They are enumerated by an ICS assay with the dominant SIINFEKL (SEQ ID NO:37) peptide that is specific for the C57BL/6 mice MHC-1 allele. The peptide was pulsed in vitro for 6 hours in the presence of brefeldin A (Golgi plug that blocks cytokine release and helps stain for these cytokines in cells) once peripheral blood mononuclear cells (PBMCs) were extracted from mouse blood. The results show that circRNA alone is more effective than positive control poly (I:C) as an adjuvant to induce OVA-specific CD8+ T cells. CircRNA with Genjet liposomes is even more effective than poly (I:C) or circRNA alone. PEI in conjunction with circRNA produces less OVA-specific CD8+ T cells. For the circRNA co-injections with liposomes, there is dose responsiveness to different amounts of RNA injected.

FIG. 9 shows a summary graph of IFN-γ secreting CD8+ T cells in mouse peripheral blood after primary and secondary vaccinations for Study #1 (Table 3). Naked circRNA or liposome-encapsulated circRNA are active in vivo. The median stimulation of circRNA and GenJet liposomes is higher than the other conditions following the primary vaccination, including poly (I:C), but there is a broad distribution pattern. While positive control poly (I:C) was the highest after secondary vaccination, circRNA alone followed as the second highest.

Figure 10:
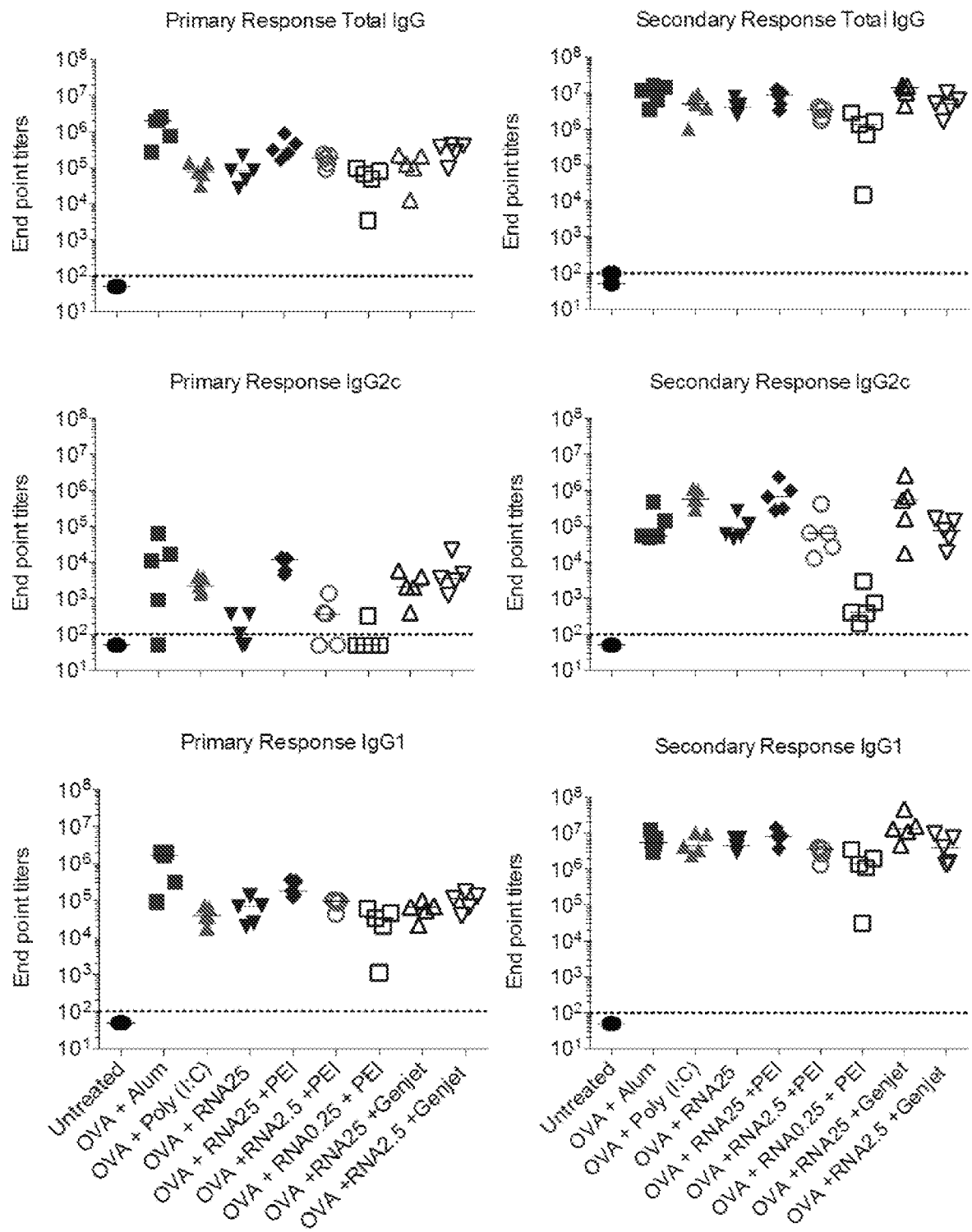
FIG. 10 shows induction of antibody response to OVA by circRNA.

FIG. 10 shows induction of antibody response to OVA by circRNA in Study #1 (Table 3). Multiple serotypes of antibodies are induced by circRNA alone or with liposomes.

FIG. 11 shows a comparison of results from Study #1 (Table 3) and Study #2 (Table 4). Both show that circRNA is effective at stimulating OVA-specific CD8+ cells in vivo. Injection of m6A-modified circRNA alone decreases the efficacy of the OVA vaccine, indicating that there is less immune stimulation from the modified circRNA. The response of MAVS KO mice to circRNA indicates that the stimulation may proceed through the MAVS pathway. While the responses are higher in Study #2 compared with Study #1, both demonstrate that circRNA alone stimulates in vivo.

The foregoing description of illustrative embodiments of the disclosure have been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of eliciting an innate-immune response in a human subject, the method comprising administering to the subject an effective amount of a circular RNA generated by splicing of an exogenous non-mammalian intron from a recombinant nucleic acid comprising: i) a 3' portion of the exogenous non-mammalian intron comprising a 3' splice site, ii) a nucleic acid sequence encoding an RNA exon, and iii) a 5' portion of the exogenous non-mammalian intron comprising a 5' splice site, wherein the exogenous non-mammalian intron is a self-splicing group I intron from a phage T4 thymidylate synthase (td) gene.

2. The method of claim 1, wherein the recombinant nucleic acid comprises a bacterial plasmid vector or a viral vector.

3. The method of claim 1, wherein the subject has cancer, an infectious disease, or an immunodeficiency.

4. The method of claim 3, wherein the infectious disease is caused by a pathogen selected from a virus, bacterium, protest, fungus and parasite.

5. The method of claim 1, wherein the method further comprises administering an antiviral agent, an antibiotic, an antifungal agent, an antiparasitic agent, a chemotherapeutic agent, or a vaccine.

6. The method of claim 1, wherein the circular RNA is administered before the subject is diagnosed with cancer, an infectious disease or an immunodeficiency.

7. The method of claim 1, wherein the circular RNA is administered after the subject is diagnosed with cancer, an infectious disease or an immunodeficiency.

8. The method of claim 1, wherein the circular RNA encodes an immunogenic polypeptide.

9. The method of claim 8, wherein the immunogenic polypeptide is derived from a cancer antigen or an organism selected from the group consisting of a bacterium, a virus, a fungus, a protest, and a parasite.

10. The method of claim 8, wherein the circular RNA is administered as a vaccine.

11. The method of claim 1, wherein the circular RNA is administered as an adjuvant.

12. The method of claim 1, wherein the circular RNA is administered as naked RNA.

13. The method of claim 1, wherein the circular RNA is administered using a lipid based carrier.

14. The method of claim 1, wherein the circular RNA is administered subcutaneously, intramuscularly or trans-dermally.

* * * * *

UNITED STATES PATENT AND TRADEMARK OFFICE
CERTIFICATE OF CORRECTION

PATENT NO. : 11,814,627 B2
APPLICATION NO. : 16/311770
DATED : November 14, 2023
INVENTOR(S) : Howard Y. Chang et al.

Page 1 of 1

It is certified that error appears in the above-identified patent and that said Letters Patent is hereby corrected as shown below:

In the Claims

Claim 4, Column 63, Lines 41-42 read:
"is caused by a pathogen selected from a virus, bacterium,
protest, fungus and parasite."

Whereas it should read:
"is caused by a pathogen selected from the group consisting of a virus, bacterium,
protist, fungus and parasite." and Claim 9, Column 64, Line 34 reads:
"fungus, a protest, and a parasite."

Whereas it should read:
"fungus, a protist, and a parasite."

Signed and Sealed this
Twenty-third Day of January, 2024

Katherine Kelly Vidal
*Director of the United States Patent and Trademark Office*